(12) United States Patent
Miyamoto et al.

(10) Patent No.: US 8,535,880 B2
(45) Date of Patent: Sep. 17, 2013

(54) ORGAN-SPECIFIC GENE, METHOD FOR IDENTIFYING THE SAME AND USE THEREOF

(75) Inventors: Saku Miyamoto, Osaka (JP); Kenji Takami, Osaka (JP); Akira Horinouchi, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 467 days.

(21) Appl. No.: 12/447,446

(22) PCT Filed: Oct. 26, 2007

(86) PCT No.: PCT/JP2007/070944
§ 371 (c)(1),
(2), (4) Date: Apr. 27, 2009

(87) PCT Pub. No.: WO2008/050870
PCT Pub. Date: May 2, 2008

(65) Prior Publication Data
US 2009/0311701 A1    Dec. 17, 2009

(30) Foreign Application Priority Data
Oct. 27, 2006   (JP) ................................ 2006-293324

(51) Int. Cl.
*C12Q 1/68* (2006.01)
(52) U.S. Cl.
USPC ........................................................ 435/6.1
(58) Field of Classification Search
None
See application file for complete search history.

(56) References Cited

U.S. PATENT DOCUMENTS
2009/0048116 A1    2/2009   Miyajima et al.

FOREIGN PATENT DOCUMENTS
JP    2004-135552 A    5/2004
WO    2004/011618 A2   2/2004

OTHER PUBLICATIONS

Deb et al., Reliable classification of two-class cancer data using evolutionary algorithms, BioSystems 72 (2003) 111-129.*
Saito-Hismintao et al. (DNA Res. Apr. 30, 2002;9(2):35-45).*
Miyamoto et al. "Development of custom DNA microarray for cynomolgus monkey and analysis of highly expressing genes in various organs." The Journal of Toxicological Sciences, vol. 31, Supplement, 2006, p. S168 and English-language translation thereof.
"Gene Logic to Idenshi Hatsugen Kaiseki System no Hanbai ni Kanshite Keiyaku Teiketsu." Sep. 9, 2005, [retrieval date: Nov. 7, 2007]   Internet<URL:http://www.gelifesciences.co.jp/company/press/20050909.asp>.

Ringwald et al. "GXD: a Gene Expression Database for the laboratory mouse." Nucleic Acids Research, 1999, vol. 27, No. 1, pp. 106-112. Oxford University Press (1999).
Celis et al. "Gene Expression Profiling: Monitoring Transcription and Translation Products Using DNA Microarrays and Proteomics." FEBS Letter 480 (2000) 23892, pp. 2-16.
Skrabanek et al. "TissueInfo: High-Throughput Identification of Tissue Expression Profiles and Specificity." Nucleic Acids Research, 2001, vol. 29, No. 21, e102, pp. 1-8. Oxford University Press (2001).
Pao et al. "In Silico Identification and Comparative Analysis of Differentially Expressed Genes in Human and Mouse Tissues." BMC Genomics 2006, vol. 7, No. 86, pp. 1-11.
Ferguson et al. "eXPRESSION: An in silico tool to predict patterns of gene expression." Gene Expression Patterns, 2005, vol. 5, pp. 619-628.
International Search Report.
Extended European Search Report issued for European Application No. 07 83 0678, dated Jun. 8, 2010.
Shyamsundar et al., "A DNA Microarray Survey of Gene Expression in Normal Human Tissues", Genome Biology, Biomed Central Ltd., vol. 6, No. 3, Feb. 14, 2005.
Son et al., "Database of mRNA Gene Expression Profiles of Multiple Human Organs", Genome Research, Mar. 2005, pp. 443-450, vol. 15, No. 3, Cold Spring Harbor Laboratory Press.
Giordano et al., "Organ-specific Molecular Classification of Primary Lung, Colon, and Ovarian Adenocarcinomas Using Gene Expression Profiles", The American Journal of Pathology, Oct. 2001, pp. 1231-1238, vol. 159, No. 4.
Higgins et al., "Gene Expression in the Normal Adult Human Kidney Assessed by Complementary DNA Microarray", Molecular Biology of the Cell, Feb. 2004, pp. 649-656, vol. 15, No. 2.
Jeffery et al., "Comparison and Evaluation of Methods for Generating Differentially Expressed Gene Lists from Microarray Data", BMC Bioinformatics, Jul. 26, 2006, vol. 7, No. 1, p. 359.
Wei et al., "Sample Size for Detecting Differentially Expressed Genes in Microarray Experiments", BMC Genomics, Nov. 8, 2004, vol. 5, No. 1, p. 87.
"Gene Logic to Idenshi Hatsugen Kaiseki System no Hanbai ni Kanshite Keiyaku Teiketsu." Sep. 9, 2005, [retrieval date: Nov. 7, 2007],   Internet<URL:http://www.gelifesciences.co.jp/company/press/20050909.asp>?
International Search Report for PCT/JP2007/070944 dated Jan. 15, 2008.

* cited by examiner

*Primary Examiner* — Christopher M. Babic
(74) *Attorney, Agent, or Firm* — Sughrue Mion, PLLC

(57) ABSTRACT

The present invention provides a method of extracting an organ- or tissue-specific highly expressed gene, including:
(1) a step for measuring expression level of a specified gene group for each organ or tissue in 2 or more individuals,
(2) a step for acquiring (a) a minimum value of expression levels in a particular organ or tissue in all individuals, and (b) a maximum value of expression levels in other organs and tissues in all individuals, for each gene, and
(3) a step for extracting the gene as a gene highly expressed specifically in the particular organ or tissue if the above-described (a)/(b) ratio is larger than 1. By the present invention, truly organ- or tissue-specific genes are extracted.

8 Claims, 6 Drawing Sheets

(A)

(B)

ORGAN-SPECIFIC GENE, METHOD FOR IDENTIFYING THE SAME AND USE THEREOF

CROSS-REFERENCE TO RELATED APPLICATION

This application is a 371 of PCT/JP2007/070944, filed Oct. 26, 2007; the entire disclosure of which is incorporated herein by reference.

TECHNICAL FIELD

The present invention relates to a method of identifying organ- or tissue-specific highly expressed genes of various organisms, a set of mouse organ- or tissue-specific highly expressed genes obtained by the method, and a method of identifying an organ or tissue for which no specific highly expressed gene has been obtained, by combining organ- or tissue-specific highly expressed genes identified by the method.

BACKGROUND OF THE INVENTION

In recent years, there has been remarkable progress in regenerative medicine (medical practice). Since a method of establishing human embryonic stem cells (ES cells) was developed, it has been a realistic goal to produce cells/tissues, and even organs themselves, for transplantation from ES cells, as well as from somatic stem cells, including mesenchymal stem cells (MSCs), on an industrial scale using approaches based on cell engineering/embryological engineering. In fact, for the blood, nerves, heart muscle, liver, pancreas and the like, a system for differentiation induction from ES cells is being developed, and a therapeutic technique using ES cells has already been reported.

Meanwhile, an evaluation of the toxicity of a drug to various organs is normally performed by an in vivo toxicity study by compound administration to laboratory animals such as rats; however, such studies are faulty in that (1) several days to several months are taken before onset of the toxicity, (2) a large amount of compound is required, (3) much costs are taken to purchase and maintain laboratory animals, and the like, and, in addition, the radical problem arises that the toxicity in humans is not always reflected.

To quickly predict the presence or absence of toxicity and efficiently optimize a structure in the initial stage of development of a pharmaceutical compound, it is essential to construct an in vitro screening system. In in vitro screening, it is common practice to use a primary culture of a tissue isolated from various organs or a cell line established therefrom; however, primary culture involves the above-described drawback (3) as with in vivo studies; meanwhile, when a cell line is used, problems arise, including the disappearance of the characteristics of the organ or tissue from which the cell line is derived during repeated passage, and the inability to fully reflect the pathology of the organ or tissue as an organic integration thereof on the basis of individual cells. For these reasons, use of a human cell does not always accurately reflect the toxicity in human individuals.

Therefore, there is a major demand for the utilization of tissues/organs that have developed as a result of differentiation induction from stem cells, including ES cells, for toxicity evaluations.

Confirmation of differentiation from stem cells such as ES cells into various cells is usually achieved by, in addition to morphological examination, detecting a product of a gene expressed specifically in the differentiated cell (i.e., differentiation marker gene) at a transcription level (e.g., RT-PCR, microarray analysis and the like) or a translation level (e.g., immunohistological staining and the like). For example, hepatocyte differentiation markers include the albumin gene and the like, and pancreatic β cell differentiation markers include the insulin gene and the like. However, differentiation into albumin-producing cells or insulin-producing cells, if confirmed, does not immediately lead to the conclusion that they are hepatocytes or pancreatic β cells. In fact, a report is available that ES cells were differentiated into insulin-producing cells; however, the resulting cells differed slightly from β cells.

Therefore, to determine whether or not a tissue/organ differentiated from a stem cell such as an ES cell reflects the physiological state of a desired tissue or organ, i.e., whether or not the tissue or organ is exactly the desired tissue or organ, it seems important to comprehensively analyze the expression of a large number of differentiation marker genes, rather than to rely on the expression of a single or several kinds of differentiation marker genes.

Some sets of various tissue/organ-specific genes that can serve as differentiation marker genes have been reported (for example, for human tissue-specific gene sets, see the patent document 1 and the like). However, there are a variety of definitions (criteria) for a specific gene, which have not been unified. For example, the present inventors previously announced that they extracted a crab-eating macaque tissue/organ-specific gene group from results of a comprehensive gene expression analysis in various organs using an independently developed crab-eating macaque DNA microarray (non-patent document 1), wherein a gene whose expression level in a specified tissue (organ) exceeded [the median (50% value) of the expression level in each other tissue/organ]+ [75% value of the expression level in the each other tissue/organ×2] was extracted as a gene highly expressed specifically in the specified tissue (organ). This method of extraction, as a means for comprehensively identifying tissue/organ-specific genes, was better than conventionally known methods; however, even so, the specific highly expressed genes extracted by the method sometimes included those that cannot be said to be truly specific for the tissue (organ).

Patent document 1: JP-A-2004-135552
Non-patent document 1: The Journal of Toxicological Science, Vol. 31 Supplement, page S168, 2006, Title: Development of crab-eating macaque DNA microarray and search for organ-specific highly expressed genes

DISCLOSURE OF THE INVENTION

Problems to Be Solved by the Invention

Accordingly, it is an object of the present invention to provide a method enabling the extraction of a gene group highly expressed truly specifically in a specified tissue or organ, and hence to provide a set of genes highly expressed specifically in the tissue or organ that are useful as differentiation marker genes in regenerative medicine and the like.

Means of Solving the Problems

The present inventors, with the aim of accomplishing the above object, diligently conducted analyses with the use of mouse gene expression data provided by GENE LOGIC™, and found that only a set of genes that are truly specific for a particular organ (tissue) can be acquired by obtaining data on the expression levels of a specified gene group for each organ or tissue in 2 or more individuals, and extracting a certain gene from the gene group as a gene highly expressed specifically in the particular organ (tissue), if the ratio of (a) a minimum value of expression level in the particular organ (tissue) and (b) a maximum value of expression levels in other organs and tissues ((a)/(b)) is larger than 1 in an individual examined for the gene.

Furthermore, the present inventors found that even for an organ or tissue from which no specific highly expressed gene is extracted by the above-described method (referred to as "organ A"), an unidentified organ (tissue) can be identified as the organ A by extracting a gene, if any, wherein the ratio of (a) a minimum value of expression level in the organ A and the expression level in another organ or tissue from which a specific highly expressed gene (referred to as "gene X") has been extracted (referred to as "organ B") and (b) a maximum value of expression levels in organs and tissues other than the organs A and B is larger than 1 in an individual examined, as a gene highly expressed specifically in the organs A and B (referred to as "gene Y"), measuring the expression levels of the genes X and Y in the unidentified organ (tissue), and demonstrating that the expression of the gene X is under the reference value and the expression of the gene Y exceeds the reference value.

The present inventors conducted further investigations based on these findings, demonstrated that in rats, dogs and humans as well, it is possible to extract a set of genes highly expressed specifically in an organ (tissue), and identify an organ (tissue) from which a combination of specific highly expressed genes comprising the set of gene is not extracted, and developed the present invention.

Accordingly, the present invention provides:

[1] a method of extracting an organ- or tissue-specific highly expressed gene, comprising the steps (1) to (3) below;
(1) measuring expression levels of a specified gene group for each organ or tissue in 2 or more individuals,
(2) acquiring, for each gene, (a) a minimum value of expression levels of a particular organ or tissue in all individuals and (b) a maximum value of expression levels in other organs and tissues in all individuals,
(3) extracting the gene as a gene highly expressed specifically in the particular organ or tissue if the above-described (a)/(b) ratio is larger than 1,

[2] the method described in [1] above, wherein the gene is extracted as a gene highly expressed specifically in a particular organ or tissue if the (a)/(b) ratio is 2 or more;

[3] a method of identifying an organ or tissue from which no specific highly expressed gene is extracted by the method described in [1] above, comprising the steps shown below;
(1) acquiring, for each gene, (a) a minimum value of expression levels in the organ or tissue and the expression levels in another particular organ or tissue in which a specific highly expressed gene is present, in all individuals, and (b) a maximum value of expression levels in organs and tissues other than each organ or tissue (a) above, in all individuals,
(2) extracting the gene as a gene highly expressed specifically in each organ or tissue (a) above if the above-described (a)/(b) ratio is larger than 1,
(3) measuring expression levels of (i) a gene highly expressed specifically in the other particular organ or tissue and (ii) the specific highly expressed gene extracted in the above-described (2) in an unidentified organ or tissue,
(4) identifying the unidentified organ or tissue as an organ or tissue from which the specific highly expressed gene is not extracted, with the expression levels of the specific highly expressed genes of the above-described (i) and (ii) as indexes,

[4] the method described in [3] above, wherein the organ or tissue is derived from a mammal;

[5] the method described in [4] above, wherein the organ or tissue is derived from a human or mouse;

[6] an analytical tool for the expression of mouse fat tissue specific genes, comprising 1 or more selected from among 35 kinds of nucleic acids comprising the same or substantially the same base sequence as each base sequence shown by SEQ ID NO:n (n is an integer of 1 to 35) or a partial sequence thereof;

[7] an analytical tool for the expression of mouse urinary bladder specific genes, comprising 1 or more selected from among 36 kinds of nucleic acids comprising the same or substantially the same base sequence as each base sequence shown by SEQ ID NO:n (n is an integer of 36 to 71) or a partial sequence thereof;

[8] an analytical tool for the expression of mouse blood specific genes, comprising 1 or more selected from among 431 kinds of nucleic acids comprising the same or substantially the same base sequence as each base sequence shown by SEQ ID NO:n (n is an integer of 72 to 502) or a partial sequence thereof;

[9] an analytical tool for the expression of mouse bone specific genes, comprising 1 or more selected from among 6 kinds of nucleic acids comprising the same or substantially the same base sequence as each base sequence shown by SEQ ID NO:n (n is an integer of 503 to 508) or a partial sequence thereof;

[10] an analytical tool for the expression of mouse brain specific genes, comprising 1 or more selected from among 246 kinds of nucleic acids comprising the same or substantially the same base sequence as each base sequence shown by SEQ ID NO:n (n is an integer of 509 to 754) or a partial sequence thereof;

[11] an analytical tool for the expression of mouse mammary gland specific genes, comprising 1 or more selected from among 17 kinds of nucleic acids comprising the same or substantially the same base sequence as each base sequence shown by SEQ ID NO:n (n is an integer of 755 to 771) or a partial sequence thereof;

[12] an analytical tool for the expression of mouse colon specific genes, comprising 1 or more selected from among 52 kinds of nucleic acids comprising the same or substantially the same base sequence as each base sequence shown by SEQ ID NO:n (n is an integer of 772 to 823) or a partial sequence thereof;

[13] an analytical tool for the expression of mouse esophagus specific genes, comprising a nucleic acid comprising the same or substantially the same base sequence as the base sequence shown by SEQ ID NO:824 or a partial sequence thereof, and/or a nucleic acid comprising the same or substantially the same base sequence as the base sequence shown by SEQ ID NO:825 or a partial sequence thereof;

[14] an analytical tool for the expression of mouse heart specific genes, comprising 1 or more selected from among 23 kinds of nucleic acids comprising the same or substantially the same base sequence as each base sequence shown by SEQ ID NO:n (n is an integer of 826 to 848) or a partial sequence thereof;

[15] an analytical tool for the expression of mouse liver specific genes, comprising 1 or more selected from among 144 kinds of nucleic acids comprising the same or substantially the same base sequence as each base sequence shown by SEQ ID NO:n (n is an integer of 849 to 992) or a partial sequence thereof;

[16] an analytical tool for the expression of mouse lung specific genes, comprising 1 or more selected from among 143 kinds of nucleic acids comprising the same or substantially the same base sequence as each base sequence shown by SEQ ID NO:n (n is an integer of 993 to 1135) or a partial sequence thereof;

[17] an analytical tool for the expression of mouse pancreas specific genes, comprising 1 or more selected from among 2970 kinds of nucleic acids comprising the same or substantially the same base sequence as each base sequence shown by SEQ ID NO:n (n is an integer of 1136 to 4105) or a partial sequence thereof;

[18] an analytical tool for the expression of mouse spleen specific genes, comprising 1 or more selected from among 195 kinds of nucleic acids comprising the same or substantially the same base sequence as each base sequence shown by SEQ ID NO:n (n is an integer of 4106 to 4300) or a partial sequence thereof;

[19] an analytical tool for the expression of mouse stomach specific genes, comprising 1 or more selected from among 29 kinds of nucleic acids comprising the same or substantially the same base sequence as each base sequence shown by SEQ ID NO:n (n is an integer of 4301 to 4329) or a partial sequence thereof;

[20] an analytical tool for the expression of mouse testis specific genes, comprising 1 or more selected from among 4669 kinds of nucleic acids comprising the same or substantially the same base sequence as each base sequence shown by SEQ ID NO:n (n is an integer of 4330 to 8998) or a partial sequence thereof;

[21] an analytical tool for the expression of mouse thymus specific genes, comprising 1 or more selected from among 141 kinds of nucleic acids comprising the same or substantially the same base sequence as each base sequence shown by SEQ ID NO:n (n is an integer of 8999 to 9139) or a partial sequence thereof;

[22] an analytical tool for the expression of mouse kidney specific genes, comprising 1 or more selected from among 66 kinds of nucleic acids comprising the same or substantially the same base sequence as each base sequence shown by SEQ ID NO:n (n is an integer of 9140 to 9205) or a partial sequence thereof;

[23] an analytical tool for the expression of mouse pancreas and prostate specific genes, comprising a nucleic acid comprising the same or substantially the same base sequence as the base sequence shown by SEQ ID NO:9206 or a partial sequence thereof; and the like.

Effect of the Invention

According to the method of extraction of the present invention, it is possible to extract a set of genes that are highly expressed truly specifically in an organ or tissue. The set of genes highly expressed specifically in an organ (tissue) thus obtained are useful as an organ or tissue differentiation marker. Furthermore, according to the method of identification of the present invention, it is possible to identify an organ or tissue for which no specific highly expressed gene has been obtained.

DETAILED DESCRIPTION OF THE INVENTION

Figure 1:
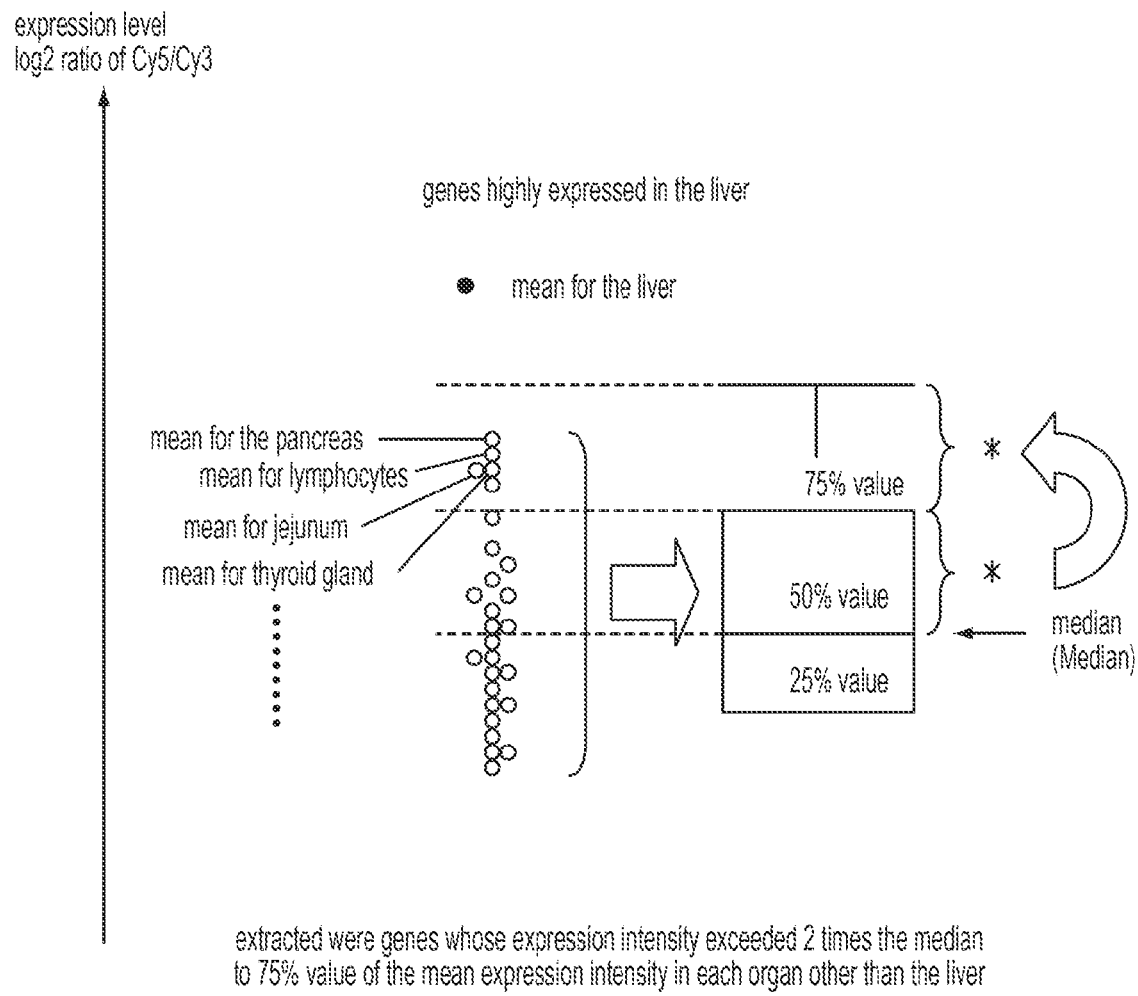
[FIG. 1] A graph showing an outline of a method of extracting organ/tissue-specific genes described in the non-patent document 1.

The present invention provides a novel method of extracting an organ- or tissue-specific highly expressed gene. The method comprises the steps (1) to (3) shown below:

(1) a step for measuring expression levels of a specified gene group for each organ or tissue in 2 or more individuals;

(2) a step for acquiring (a) a minimum value of expression levels in a particular organ or tissue in all individuals, and (b) a maximum value of expression levels in other organs and tissues in all individuals, for each gene; and (3) a step for extracting the gene as a gene highly expressed specifically in the particular organ or tissue if the above-described (a)/(b) ratio is larger than 1.

The subject to which the method of extraction of the present invention is applicable is not particularly limited, as far as it is an organism consisting of 2 or more differentiated tissues, preferably higher animals and plants, more preferably mammals (e.g., humans, monkeys, cattle, horses, pigs, sheep, goats, rabbits, mice, rats, guinea pigs, hamsters and the like), birds such as chickens and domesticated ducks, and the like can be mentioned. Particularly preferred are humans and mice.

The number of organism individuals subjected to the measuring method of the present invention is not particularly limited, as far as it is 2 or more; the expression levels of a gene group are examined for each organ or tissue preferably in 3 or more, more preferably 5 or more, and particularly preferably 10 or more, individuals.

The organ or tissue to be a subject of measurement varies depending on the organism being the subject; in the case of mammals, examples include, but are not limited to, fat tissue, urinary bladder, blood, femoral bone, brain, spinal cord, hypophysis, thyroid, gallbladder, bone marrow, adrenal, skin, blood vessels, mammary gland, colon, esophagus, heart, kidney, liver, lung, pancreas, prostate, skeletal muscle, spleen, stomach, testis, thymus, ovary, placenta, uterus and the like.

Each organ and tissue are obtained by, for example, euthanizing a laboratory animal such as a mouse or a rat by a conventional method, and resecting and isolating the organ and tissue. Meanwhile, for humans, except for some tissues, including blood, no organ or tissue can be collected from a normal living body, so organs and tissues are collected from a deceased individual, patient and the like; in the case of death from disease (illness), a disease-specific change in the expression of a gene is anticipated, so it is desirable, for example, that organs and tissues be collected from a person not suffering from a disease, such as a victim of a traffic accident.

The expression of a specified gene group in an organ or tissue collected can be examined by preparing an RNA (e.g., total RNA, mRNA) fraction from the organ or tissue, and detecting a transcription product of the gene group contained in the fraction. Preparation of an RNA fraction can be performed using a publicly known technique such as the guanidine-CsCl ultracentrifugation method, the AGPC method or the like; a highly pure total RNA can be prepared from a very small amount of sample quickly and conveniently using a commercially available kit for RNA extraction (e.g., RNeasy Mini Kit; manufactured by QIAGEN™, and the like).

As a specified gene group whose expression level is measured in the method of extraction of the present invention, the whole set of genes known to be expressed in the organism being the subject can be mentioned. The number of genes contained in the gene group varies depending on the biological species being the subject, and is, for example, in the case of a mammal such as a human, mouse, rat, or monkey, about 5,000 to about 30,000. For various mammals such as humans, mice, rats, crab-eating macaques, and rhesus monkeys, DNA chips (microarrays) equipped with a probe set for analyzing the expression of such a gene group are commercially available (for example, one manufactured by AFFYMETRIX™ and the like), and they can be utilized.

For example, a cDNA incorporating an appropriate promoter such as the T7 promoter is synthesized from an RNA fraction prepared as described above, by a reverse transcription reaction, and further a cRNA is synthesized using RNA polymerase (in this operation, with the use of a mononucleotide labeled with biotin or the like as the substrate, a labeled cRNA is obtained). By bringing this labeled cRNA into contact with the above-described DNA microarray to cause a hybridization reaction, and measuring the amount of label bound to each probe on the array, the expression level of each gene can be measured.

For example, for humans, mice, rats and the like, analytical data on the expression of gene groups in various organs and tissues acquired using the above-described DNA microarray have been available in databases for restricted access (for example, from GENE LOGIC™ and the like); for such biological species, by accessing the database, and analyzing the data therein, without actually performing a measurement of gene expression as described above, organ- or tissue-specific genes (set) can also be extracted.

As described above, data on the expression level of a specified gene group (for example, the respective genes are given the numbers 1 to n) for each organ or tissue in each individual (number of individuals=m) are obtained.

Next, for a certain gene i out of them, if the ratio of (a) a minimum value of expression levels in a certain organ or tissue A (EXP 1(i/A), ... EXP m(i/A)) (Min[EXP 1–m(i/A)]) and (b) a maximum value of expression levels of the gene i in other organs and tissues (for example, B to Z) (Max[EXP 1–m(i/B–Z)]) ((a)/(b)) is larger than 1 in all individuals examined, the gene i is extracted as a gene highly expressed specifically in the organ or tissue A.

By performing the above-described operation on gene 1 to gene n for each of the organs or tissues A to Z, a set of genes highly expressed specifically in each organ or tissue is extracted.

The (a)/(b) ratio is not particularly limited, as far as it is larger than 1, and it can be set at an optionally chosen level. The higher the value is set, the higher the organ (tissue) specificity is; however, having an excessively high setting is faulty in that no specific highly expressed gene is extracted in many organs (tissues). Preferably, the (a)/(b) ratio can be selected as appropriate in the range of 1.5 or more to 16 or more, more preferably 2 or more to 8 or more.

By the above-described method of extraction (the (a)/(b) ratio was set at 2 or more), (M1) 35 kinds of mouse fat tissue-specific highly expressed genes comprising the base sequences shown by SEQ ID NO:1 to 35, respectively, (M2) 36 kinds of mouse urinary bladder-specific highly expressed genes comprising the base sequences shown by SEQ ID NO:36 to 71, respectively, (M3) 431 kinds of mouse blood-specific highly expressed genes comprising the base sequences shown by SEQ ID NO:72 to 502, respectively, (M4) 6 kinds of mouse bone-specific highly expressed genes comprising the base sequences shown by SEQ ID NO:503 to 508, respectively, (M5) 246 kinds of mouse brain-specific highly expressed genes comprising the base sequences shown by SEQ ID NO:509 to 754, respectively, (M6) 17 kinds of mouse mammary gland-specific highly expressed genes comprising the base sequences shown by SEQ ID NO:775 to 771, respectively, (M7) 52 kinds of mouse colon-specific highly expressed genes comprising the base sequences shown by SEQ ID NO:772 to 823, respectively, (M8) 2 kinds of mouse esophagus-specific highly expressed genes comprising the base sequences shown by SEQ ID NO:824 to 825, respectively, (M9) 23 kinds of mouse heart-specific highly expressed genes comprising the base sequences shown by SEQ ID NO:826 to 848, respectively, (M10) 144 kinds of mouse liver-specific highly expressed genes comprising the base sequences shown by SEQ ID NO:849 to 992, respectively, (M11) 143 kinds of mouse lung-specific highly expressed genes comprising the base sequences shown by SEQ ID NO:993 to 1135, respectively, (M12) 2970 kinds of mouse pancreas-specific highly expressed genes comprising the base sequences shown by SEQ ID NO:1136 to 4105, respectively, (M13) 195 kinds of mouse spleen-specific highly expressed genes comprising the base sequences shown by SEQ ID NO:4106 to 4300, respectively, (M14) 29 kinds of mouse stomach-specific highly expressed genes comprising the base sequences shown by SEQ ID NO:4301 to 4329, respectively, (M15) 4669 kinds of mouse testis-specific highly expressed genes comprising the base sequences shown by SEQ ID NO:4330 to 8998, respectively, (M16) 141 kinds of mouse thymus-specific highly expressed genes comprising the base sequences shown by SEQ ID NO:8999 to 9139, respectively, and (M17) 66 kinds of mouse kidney-specific highly expressed genes comprising the base sequences shown by SEQ ID NO:9140 to 9205, respectively, were obtained.

Likewise, by the above-described method of extraction, (R1) 25 kinds of rat fat-specific highly expressed genes comprising the base sequences shown by SEQ ID NO:9207 to 9231, respectively, (R2) 27 kinds of rat blood-specific highly expressed genes comprising the base sequences shown by SEQ ID NO:9232 to 9258, respectively, (R3) 1 kind of rat duodenum-specific highly expressed gene comprising the base sequence shown by SEQ ID NO:9259, (R4) 4 kinds of rat thymus-specific highly expressed genes comprising the base sequences shown by SEQ ID NO:9260 to 9263, respectively (hereinabove, the (a)/(b) ratio was set at 2 or more), (R5) 3 kinds of rat colon-specific highly expressed genes comprising the base sequences shown by SEQ ID NO:9264 to 9266, respectively, (R6) 4 kinds of rat heart-specific highly expressed genes comprising the base sequences shown by SEQ ID NO:9267 to 9270, respectively (hereinabove, the (a)/(b) ratio was set at 4 or more), (R7) 5 kinds of rat adrenal-specific highly expressed genes comprising the base sequences shown by SEQ ID NO:9271 to 9275, respectively, (R8) 2 kinds of rat urinary bladder-specific highly expressed genes comprising the base sequences shown by SEQ ID NO:9276 to 9277, respectively, (R9) 4 kinds of rat cerebellum-specific highly expressed genes comprising the base sequences shown by SEQ ID NO:9278 to 9281, respectively, (R10) 1 kind of rat esophagus-specific highly expressed gene comprising the base sequence shown by SEQ ID NO:9282, (R11) 10 kinds of rat femoral bone-specific highly expressed genes comprising the base sequences shown by SEQ ID NO:9283 to 9292, respectively, (R12) 2 kinds of rat ileum-specific highly expressed genes comprising the base sequences shown by SEQ ID NO:9293 to 9294, respectively, (R13) 12 kinds of rat kidney-specific highly expressed genes comprising the base sequences shown by SEQ ID NO:9295 to 9306, respectively, (R14) 598 kinds of rat testis-specific highly expressed genes comprising the base sequences shown by SEQ ID NO:9307 to 9904, respectively, (R15) 49 kinds of rat liver-specific highly expressed genes comprising the base sequences shown by SEQ ID NO:9905 to 9953, respectively, (R16) 7 kinds of rat lung-specific highly expressed genes comprising the base sequences shown by SEQ ID NO:9954 to 9960, respectively, (R17) 11 kinds of rat mammary gland-specific highly expressed genes comprising the base sequences shown by SEQ ID NO:9961 to 9971, respectively, (R18) 33 kinds of rat pancreas-specific highly expressed genes comprising the base sequences shown by SEQ ID NO:9972 to 10004, respectively, (R19) 26 kinds of rat prostate-specific highly expressed genes comprising the base sequences shown by SEQ ID NO:10005 to 10030, respectively, (R20) 1 kind of rat skeletal muscle-specific highly expressed gene comprising the base sequence shown by SEQ ID NO:10031, (R21) 1 kind of rat spleen-specific highly expressed genes comprising the base sequence shown by SEQ ID NO:10032, (R22) 10 kinds of rat stomach-specific highly expressed genes comprising the base sequences shown by SEQ ID NO:10033 to 10042, respectively, and (R23) 2 kinds of rat submandibular lymph node-specific highly expressed genes comprising the base sequences shown by SEQ ID NO:10043 to 10044, respectively (hereinabove, the (a)/(b) ratio was set at 8 or more), were obtained.

Likewise, by the above-described method of extraction, (D1) 2 kinds of dog duodenum (mucosa)-specific highly expressed genes comprising the base sequences shown by SEQ ID NO:10056 to 10057, respectively, (D2) 5 kinds of dog stomach (mucosa)-specific highly expressed genes comprising the base sequences shown by SEQ ID NO:10058 to 10062, respectively (hereinabove, the (a)/(b) ratio was set at 2 or more), (D3) 1 kind of dog aorta-specific highly expressed gene comprising the base sequence shown by SEQ ID NO:10063, (D4) 1 kind of dog urinary bladder-specific highly expressed gene comprising the base sequence shown by SEQ ID NO:10064, (D5) 6 kinds of dog kidney (medulla)-specific highly expressed genes comprising the base sequences shown by SEQ ID NO:10065 to 10070, respectively, (D6) 1 kind of dog mesenteric lymph node-specific highly expressed gene comprising the base sequence shown by SEQ ID NO:10071 (hereinabove, the (a)/(b) ratio was set at 4 or more), (D7) 6 kinds of dog fat-specific highly expressed genes comprising the base sequences shown by SEQ ID NO:10072 to 10077, respectively, (D8) 7 kinds of dog adrenal-specific highly expressed genes comprising the base sequences shown by SEQ ID NO:10078 to 10084, respectively, (D9) 10 kinds of dog cerebral cortex-specific highly expressed genes comprising the base sequences shown by SEQ ID NO:10085 to 10094, respectively, (D10) 32 kinds of dog epididymis-specific highly expressed genes comprising the base sequences shown by SEQ ID NO:10095 to 10126, respectively, (D11) 4 kinds of dog heart-specific highly expressed genes comprising the base sequences shown by SEQ ID NO:10127 to 10130, respectively, (D12) 10 kinds of dog kidney (cortex)-specific highly expressed genes comprising the base sequences shown by SEQ ID NO:10131 to 10140, respectively, (D13) 118 kinds of dog liver-specific highly expressed genes comprising the base sequences shown by SEQ ID NO:10141 to 10258, respectively, (D14) 10 kinds of dog lung-specific highly expressed genes comprising the base sequences shown by SEQ ID NO:10259 to 10268, respectively, (D15) 90 kinds of dog pancreas-specific highly expressed genes comprising the base sequences shown by SEQ ID NO:10269 to 10358, respectively, (D16) 3 kinds of dog hypophysis-specific highly expressed genes comprising the base sequences shown by SEQ ID NO:10359 to 10361, respectively, (D17) 24 kinds of dog skeletal muscle-specific highly expressed genes comprising the base sequences shown by SEQ ID NO:10362 to 10385, respectively, (D18) 53 kinds of dog skin-specific highly expressed genes comprising the base sequences shown by SEQ ID NO:10386 to 10438, respectively, (D19) 5 kinds of dog spleen-specific highly expressed genes comprising the base sequences shown by SEQ ID NO:10439 to 10443, respectively, ($D_2O$) 12 kinds of dog stomach (mucosa)-specific highly expressed genes comprising the base sequences shown by SEQ ID NO:10444 to 10455, respectively, (D21) 11 kinds of dog submandibular lymph node-specific highly expressed genes comprising the base sequences shown by SEQ ID NO:10456 to 10466, respectively, (D22) 1303 kinds of dog testis-specific highly expressed genes comprising the base sequences shown by SEQ ID NO:10467 to 11769, respectively, (D23) 2 kinds of dog thymus-specific highly expressed genes comprising the base sequences shown by SEQ ID NO:11770 to 11771, respectively, (D24) 14 kinds of dog thyroid-specific highly expressed genes comprising the base sequences shown by SEQ ID NO:11772 to 11785, respectively, and (D25) 1 kind of dog whole ileum (mucosa+muscle)-specific highly expressed gene comprising the base sequence shown by SEQ ID NO:11786 (hereinabove, the (a)/(b) ratio was set at 8 or more), were obtained.

Likewise, by the above-described method of extraction, (H1) 17 kinds of human aorta-specific highly expressed genes comprising the base sequences shown by SEQ ID NO:11790 to 11806, respectively, (H2) 8 kinds of human hypothalamus-specific highly expressed genes comprising the base sequences shown by SEQ ID NO:11807 to 11814, respectively, (H3) 3 kinds of human right ventricle-specific highly expressed genes comprising the base sequences shown by SEQ ID NO:11815 to 11817, respectively (hereinabove, the (a)/(b) ratio was set at 2 or more), (H4) 1 kind of human urinary bladder-specific highly expressed gene comprising the base sequence shown by SEQ ID NO:11818, (H5) 19 kinds of human cerebrum-specific highly expressed genes comprising the base sequences shown by SEQ ID NO:11819 to 11837, respectively, (H6) 3 kinds of human thalamus-specific highly expressed genes comprising the base sequences shown by SEQ ID NO:11838 to 11840, respectively, (H7) 1 kind of human left ventricle-specific highly expressed gene comprising the base sequence shown by SEQ ID NO:11841 (hereinabove, the (a)/(b) ratio was set at 4 or more), (H8) 8 kinds of human osteous tissue-specific highly expressed genes comprising the base sequences shown by SEQ ID NO:11842 to 11849, respectively, (H9) 3 kinds of human cerebellum-specific highly expressed genes comprising the base sequences shown by SEQ ID NO:11850 to 11852, respectively, (H10) 12 kinds of human kidney-specific highly expressed genes comprising the base sequences shown by SEQ ID NO:11853 to 11864, respectively, (H11) 5 kinds of human liver-specific highly expressed genes comprising the base sequences shown by SEQ ID NO:11865 to 11869, respectively, (H12) 19 kinds of human lung-specific highly expressed genes comprising the base sequences shown by SEQ ID NO:11870 to 11888, respectively, (H13) 45 kinds of human pancreas-specific highly expressed genes comprising the base sequences shown by SEQ ID NO:11889 to 11933, respectively, (H14) 4 kinds of human prostate-specific highly expressed genes comprising the base sequences shown by SEQ ID NO:11934 to 11937, respectively, (H15) 14 kinds of human skeletal muscle-specific highly expressed genes comprising the base sequences shown by SEQ ID NO:11938 to 11951, respectively, (H16) 5 kinds of human skin-specific highly expressed genes comprising the base sequences shown by SEQ ID NO:11952 to 11956, respectively, (H17) 1 kind of human spleen-specific highly expressed gene comprising the base sequence shown by SEQ ID NO:11957, (H18) 10 kinds of human testis-specific highly expressed genes comprising the base sequences shown by SEQ ID NO:11958 to 11967, respectively, (H19) 10 kinds of human thyroid-specific highly expressed genes comprising the base sequences shown by SEQ ID NO:11968 to 11977, respectively, and (H20) 1 kind of human right atrium-specific highly expressed gene comprising the base sequence shown by SEQ ID NO:11978 (hereinabove, the (a)/(b) ratio was set at 8 or more) were obtained.

These organ-(tissue)-specific highly expressed genes, by analyzing the expression thereof, can be utilized for identification of an unidentified organ or tissue (differentiation marker), for evaluation of drug toxicity in a particular organ or tissue (toxicity marker candidate), and for diagnosis of a particular organ disease (disease marker candidate).

Therefore, the present invention also provides an analytical tool for the expression of organ- or tissue-specific genes of mice, rats, dogs or humans, comprising a nucleic acid comprising the same or substantially the same base sequence as the base sequence of one of the above-described organ- or tissue-specific highly expressed genes of the various animals, or a partial sequence thereof.

"Substantially the same base sequence" means a base sequence capable of hybridizing to a nucleic acid consisting of the base sequence shown by each SEQ ID NO under high stringent conditions. Here, "high stringent conditions" means a hybridization reaction at 45° C. in 6×SSC (sodium chloride/sodium citrate) followed by not less than one time of washing at 65° C. in 0.2×SSC/0.1% SDS. For example, as substantially the same base sequence as the base sequence shown by each SEQ ID NO, a base sequence having a homology of 80% or more, preferably 90% or more, more preferably 95% or more, and particularly preferably 98% or more, to the base sequence shown by each SEQ ID NO can be mentioned. Base sequence homology herein can be calculated using the homology calculation algorithm NCBI BLAST (National Center for Biotechnology Information Basic Local Alignment Search Tool) under the following conditions (expectancy=10; gap allowed; filtering=ON; match score=1; mismatch score=−3).

As each nucleic acid that constitutes the analytical tool of the present invention for the expression of organ-(tissue)-specific genes, a nucleic acid (probe) capable of hybridizing specifically to a mouse-, rat-, dog- or human-derived gene transcription product being the subject of detection, a pair of oligonucleotides (primers) capable of functioning as primers that amplify a portion or all of the transcription product and the like can be mentioned. The nucleic acid may be a DNA or an RNA, or a DNA/RNA chimera. Preferably, a DNA can be mentioned.

The nucleic acid used as a probe may be double-stranded or single-stranded. In the case of a double strand, the nucleic acid may be a double-stranded DNA, a double-stranded RNA, or a DNA/RNA hybrid. In the case of a single strand, a sense strand (e.g., in the case of cDNA or CRNA) or an antisense strand (e.g., in the case of mRNA or cDNA) can be selectively used according to the sample supplied. The length of the nucleic acid is not particularly limited, as far as the nucleic acid is capable of hybridizing specifically to a target nucleic acid; for example, the length is about 15 bases or more, preferably about 20 bases or more, and more preferably about 25 bases or more. The nucleic acid is preferably labeled with a labeling agent so as to enable the detection and quantitation of the target nucleic acid. Examples of labeling agents used are radioisotopes, enzymes, fluorescent substances, luminescent substances and the like. Examples of radioisotopes used are [$^{32}$P], [$^{3}$H], [$^{14}$C] and the like. Preferred examples of the enzymes are those that are stable and have a higher specific activity, which include β-galactosidase, β-glucosidase, alkaline phosphatase, peroxidase, malate dehydrogenase and the like. Examples of fluorescent substances used include fluorescamine, fluorescein isothiocyanate and the like. Examples of luminescent substances used are luminol, a luminol derivative, luciferin, lucigenin and the like. Furthermore, a biotin-(strepto)avidin system may be used as well for binding a probe and a labeling agent. Meanwhile, when a nucleic acid to be a probe is immobilized on a solid phase, the nucleic acid in the sample can be labeled using the same labeling agent as that described above.

A set of oligonucleotides used as primers is not particularly limited, as far as they are capable of hybridizing specifically to a sense strand and antisense strand, respectively, of the mouse-derived gene transcription product comprising the base sequence shown by each SEQ ID NO, and capable of amplifying the DNA fragment sandwiched therebetween; for example, a set of oligo-DNAs each having a length of about 15 to about 100 bases, preferably about 15 to about 50 bases, and designed to amplify a DNA fragment about 100 bp to several kbp long, can be mentioned.

A nucleic acid that functions as a probe capable of detecting a mouse-, rat-, dog- or human-derived organ (tissue)-specific gene transcription product can be acquired by amplifying a nucleic acid of desired length by a PCR method using the above-described primer set capable of amplifying a portion or all of the transcription product of the gene, with a cDNA or genomic DNA derived from the organ (tissue) of any of the aforementioned animals as the template, or by cloning the above-described organ-(tissue)-specific highly expressed gene or cDNA from the organ-(tissue)-derived cDNA or genomic DNA library by colony or plaque hybridization and the like, and using as required a restriction endonuclease and the like, to obtain a fragment of appropriate length. The hybridization can be performed according to, for example, a method described in MOLECULAR CLONING, 2nd edition and the like. When a commercially available library is used, hybridization can be performed according to the method described in the instruction manual attached to the library. Alternatively, the nucleic acid can be obtained by chemically synthesizing a portion or all of the base sequence and/or a sequence complementary thereto using a commercially available automated DNA/RNA synthesizer and the like, on the basis of base sequence information on each of the products of mouse-, rat-, dog- or human-derived organ-(tissue)-specific highly expressed genes (for example, in the case of mouse, the base sequences shown by SEQ ID NO:1 to 9205). By directly synthesizing the nucleic acid in situ (on chip) on a solid phase such as silicon or glass and the like, it is also possible to prepare a chip (array) on which the nucleic acid is immobilized.

The analytical tool of the present invention for the expression of genes specific for various mouse, rat, dog or human organs (tissues) comprises a set of nucleic acids capable of detecting a transcription product of at least 1 kind, preferably 2 kinds or more, of genes selected from the group consisting of genes highly expressed specifically in the various organs (tissues) of the aforementioned various animals. The analytical tool may comprise, in addition to the set of nucleic acids, as an internal standard, 1 kind or more of nucleic acids comprising the same or substantially the same base sequence as the base sequence of the transcription product of the mouse housekeeping gene, or a partial sequence thereof. Here, "substantially the same base sequence" is as defined above. Examples of mouse housekeeping genes include, but are not limited to, β-actin, GAPDH, hexokinase, histone and the like.

These nucleic acids may be supplied in a dry state or a state of alcohol precipitate as a solid, and may be supplied in a state dissolved in water or an appropriate buffer solution (e.g., TE buffer solution and the like). When used as a probe, the nucleic acid may be supplied in a state previously labeled with any one of the above-described labeling substances, and may be supplied separately from a labeling substance and labeled before use.

Alternatively, the nucleic acid can be supplied in a state immobilized on an appropriate solid phase. Examples of solid phases include, but are not limited to, glass, silicon, plastics, nitrocellulose, nylon, polyvinylidene difluoride and the like.

Means of immobilization include, but are not limited to, a method wherein a functional group such as an amino group, an aldehyde group, an SH group or biotin is previously introduced into a nucleic acid, meanwhile, a functional group capable of reacting with the nucleic acid (e.g., aldehyde group, amino group, SH group, streptavidin and the like) is introduced onto a solid phase, and bridging the solid phase and the nucleic acid by the covalent bond between the two functional groups, or a solid phase is coated with a polycation to immobilize a polyanionic nucleic acid by means of an electrostatic bond.

As an example of a preferred embodiment wherein a nucleic acid probe is supplied in a state immobilized on a solid phase, a DNA microarray can be mentioned. A DNA microarray can be prepared by either the AFFYMETRIX™ method, wherein a nucleic acid probe is synthesized for each nucleotide on a substrate (glass, silicon and the like), or the Stanford method, wherein a previously prepared nucleic acid probe is spotted onto a substrate.

To quantitatively analyze the expression of a mouse, rat, dog or human organ-(tissue)-specific gene using a very small amount of RNA sample, it is preferable to use competitive RT-PCR or real-time RT-PCR. Competitive RT-PCR refers to a method wherein a known amount of another template nucleic acid that can be amplified by a set of primers capable of amplifying a desired DNA, as a competitor, is allowed to be present in the reaction liquid, to competitively cause an amplification reaction, and comparing the amount of amplification product, whereby the amount of the desired DNA is calculated. Therefore, when competitive RT-PCR is used, the reagent of the present invention can further comprise, in addition to the above-described primer set, a nucleic acid that is amplified by the primer set to produce an amplification product distinguishable from the desired DNA (for example, an amplification product having a size different from that of the desired DNA, and exhibiting a different migration pattern after restriction endonuclease treatment, and the like). This competitor nucleic acid may be a DNA or an RNA. In the case of a DNA, a cDNA is synthesized from an RNA sample by a reverse transcription reaction, and thereafter a competitor is added, and a PCR is performed; in the case of an RNA, the competitor may be added to the RNA sample in advance and RT-PCR can be performed. In the latter case, because the efficiency of the reverse transcription reaction is also taken into account, the absolute amount of the original mRNA can be estimated.

Meanwhile, because real-time RT-PCR enables monitoring of the amount amplified in PCR in real time, it does not require electrophoresis, and makes it possible to more quickly analyze the expression of a mouse organ-(tissue)-specific gene. Usually, monitoring is performed using various fluorescent reagents. These reagents include a reagent that emits fluorescence by binding to a double-stranded DNA (intercalater), such as SYBR Green I and ethidium bromide, as well as a nucleic acid that can be used as the above-described probe (provided that the nucleic acid hybridizes to the target nucleic acid in the amplification region), modified at both ends thereof with a fluorescent substance (e.g., FAM, HEX, TET, FITC and the like) and a quenching substance (e.g., TAMRA, DABCYL and the like), respectively, and the like.

The present invention also provides a method of analyzing gene expression in a mouse, rat, dog or human, comprising measuring a gene transcription product in a sample derived from any one of the animals using 1 kind or more of the above-described gene analytical tools of the present invention.

For example, a gene analytical tool of the present invention can be used preferably to detect and identify a disease marker gene, a pharmacological action marker gene or a drug toxicity marker gene using various organ samples collected from a disease model animal (mouse, rat, dog) or a drug-dosed animal (mouse, rat, dog or human), or a drug-exposed primary culture of an animal tissue or a culture or established cell derived therefrom, and the like, and to analyze disease mechanisms, pharmacological action mechanisms, and toxicological action mechanisms.

Gene expression in an organ (tissue) sample collected from a mouse, rat, dog or human or a drug-exposed mouse, rat, dog or human cell/tissue sample can be examined by preparing an RNA (e.g., total RNA, mRNA) fraction from the sample, and detecting a transcription product of the marker gene contained in the fraction. Preparation of an RNA fraction can be performed using a publicly known technique such as the guanidine-CsCl ultracentrifugation method, the AGPC method or the like; a highly pure total RNA can be prepared quickly and conveniently from a very small amount of sample using a commercially available kit for RNA extraction (e.g., RNeasy Mini Kit; manufactured by QIAGEN™, and the like). As examples of means of detecting a gene transcription product in an RNA fraction, a method using hybridization (Northern blot, dot blot, DNA chip (microarray) analysis and the like), or a method using a PCR (RT-PCR, competitive PCR, real-time PCR and the like) and the like can be mentioned. Preference is given to quantitative PCR methods such as competitive PCR and real-time PCR because of the ability to detect gene expression changes in a very small amount of sample quickly and conveniently with high accuracy, and to DNA chip (microarray) analysis because of the ability to detect expression changes in a plurality of marker genes at one time, and of the possibility of improving the accuracy by choosing appropriate method of detection and the like.

When Northern blot or dot blot hybridization is used, detection of gene expression can be achieved using the above-described gene analytical tool of the present invention comprising a nucleic acid used as a labeled probe. Specifically, when Northern hybridization is used, by separating an RNA fraction prepared as described above by gel electrophoresis, thereafter transferring the fraction to a membrane such as of nitrocellulose, nylon, or polyvinylidene difluoride, and hybridizing the fraction in a hybridization buffer solution containing the reagent of the present invention or each reagent contained in the kit of the present invention under the above-described "high stringent conditions" and thereafter measuring the amount of label bound to the membrane by an appropriate method for each band, the expression level of each gene can be measured. In the case of dot blot as well, by subjecting a membrane with an RNA fraction spotted thereon to a hybridization reaction in the same manner (performed for each gene), and measuring the amount of label in the spot, the expression level of each gene can be measured.

In the case of DNA chip (microarray) analysis, for example, a cDNA incorporating an appropriate promoter such as the T7 promoter is synthesized from an RNA fraction prepared as described above, by a reverse transcription reaction, and a cRNA is synthesized using RNA polymerase (in this operation, with the use of a mononucleotide labeled with biotin or the like as the substrate, a labeled cRNA is obtained). By bringing this labeled cRNA into contact with the above-described immobilized probe to cause a hybridization reaction, and measuring the amount of label bound to each probe on the solid phase, the expression level of each gene can be measured. The method is increasingly advantageous in terms of rapidity and convenience with the increase in the number of genes detected (hence the number of probes immobilized).

Furthermore, the present invention provides a novel method of identification, even for an organ or tissue from which no specific highly expressed gene is extracted by the above-described method of extraction of the present invention (referred to as A), that makes it possible to identify an unidentified organ or tissue as an organ or tissue A from which the specific highly expressed gene is not extracted.

First, for a certain gene i (i=1 to n), if the ratio of (a) a minimum value of expression levels in the organ or tissue A (EXP 1(i/A), ... EXP m(i/A)) and the expression levels in an organ or tissue from which a set X of specific highly expressed genes has been obtained (referred to as B) (EXP 1(i/B), ... EXP m(i/B)) (Min[EXP 1–m(i/A,B)]), and (b) a maximum value of expression levels of the gene i in organs and tissues other than the organs A and B (for example, C to Z) (Max[EXP 1–m(i/C–Z)]) ((a)/(b)) in all individuals examined (number of individuals=m) is larger than 1, the gene i is extracted as a gene highly expressed specifically in the organs or tissues A and B. By performing this operation for the genes 1 to n, a set Y of genes highly expressed specifically in the organs or tissues A and B is obtained. Here, there is absolutely no overlap between the genes contained in the set X and the genes contained in the set Y. The (a)/(b) ratio, as with the above-described method of extraction of the present invention, can be set at any value chosen as appropriate in the range of not less than 1, preferably 1.5 or more to 16 or more, and more preferably 2 or more to 8 or more.

Next, the expression levels of 1 kind or more genes contained in the set X of genes highly expressed specifically in the organ or tissue B (for example, including genes $x_1$, $x_2$, ... $x_p$) and the expression levels of 1 kind or more genes contained in the set Y of genes highly expressed specifically in the organs or tissues A and B (for example, including genes $y_1$, $y_2$, ... $y_q$), in an unidentified organ or tissue, are measured. The unidentified organ or tissue is not particularly limited, as far as it is derived from the biological species from which the gene groups contained in the sets X and Y are derived; an organ or tissue derived preferably from a mammal, more preferably from a human, dog, rat or mouse, can be mentioned.

As a result, if the expression of the genes contained in X is under the reference value, and the expression of the genes contained in Y is not less than the reference value, the unidentified organ (tissue) should be either the organ A or B, and should not be the organ B, so it can be identified as the organ A.

Here, the "reference value" for the expression level of each gene varies depending on the gene; for example, for a gene $x_i$ contained in the gene set X, a minimum value of expression levels in the organ or tissue B in m (m≧2, preferably m≧5, more preferably m≧10) mammal individuals (Min[EXP 1–m ($x_i$/B)]), or a maximum value of expression level of the gene in organs and tissues other than the organ B (for example, A and C to Z) (Max[EXP 1–m($x_i$/A,C–Z)]) and the like can be mentioned, the latter being more preferable. Meanwhile, for a gene $y_i$ contained in the gene set Y, a minimum value of expression level in the organ or tissue A and the expression level in the organ or tissue B (Min[EXP 1–m($y_i$/A,B)]), or a maximum value of expression level of the gene in organs and tissues other than the organs A and B (for example, C to Z) (Max[EXP 1–m($y_i$/C–Z)]), in m (m≧2, preferably m≧5, more preferably m≧10) mouse individuals and the like can be mentioned, the former being more preferable.

For example, as shown in an Example below, even when the above-described method of extraction of the present invention (the (a)/(b) ratio is 2 or more) is performed, no mouse prostate-specific highly expressed gene is obtained. However, as a gene specific for the mouse pancreas and prostate, a gene comprising the base sequence shown by SEQ ID NO:9206 is extracted. Therefore, by examining the expression of 1 kind or more genes selected from among mouse pancreas-specific highly expressed genes (2970 kinds of genes comprising the base sequences shown by SEQ ID NO:1136 to 4105, respectively) and the mouse pancreas- and prostate-specific highly expressed gene in an unidentified mouse organ or tissue, the mouse organ or tissue can be identified as the pancreas, prostate or any other one. Therefore, the present invention also provides an analytical tool for the expression of (M18) a mouse pancreas- and prostate-specific gene comprising a nucleic acid comprising the same or substantially the same base sequence as the base sequence shown by SEQ ID NO:9206 or a partial sequence thereof. Here, "substantially the same base sequence" are as defined above.

Likewise, by the method of extraction of the present invention, for rats, (R24) 1 kind of rat ileum- and jejunum-specific highly expressed gene comprising the base sequence shown by SEQ ID NO:10045, (R25) 3 kinds of rat mesenteric lymph node- and submandibular lymph node-specific highly expressed genes comprising the base sequences shown by SEQ ID NO:10046 to 10048, respectively, (R26) 1 kind of rat mesenteric lymph node-, submandibular lymph node- and thymus-specific highly expressed gene comprising the base sequence shown by SEQ ID NO:10049 (hereinabove, the (a)/(b) ratio is set at 2 or more), (R27) 1 kind of rat whole cerebral cortex (frontal lobe+parietal lobe+temporal lobe)-specific highly expressed gene comprising the base sequence shown by SEQ ID NO:10050 (the (a)/(b) ratio is 4 or more), (R28) 3 kinds of rat ileum-, jejunum- and duodenum-specific highly expressed genes comprising the base sequences shown by SEQ ID NO:10051 to 10053, respectively and (R29) 2 kinds of rat ileum-, jejunum-, duodenum- and colon-specific highly expressed genes comprising the base sequences shown by SEQ ID NO:10054 to 10055, respectively (hereinabove, the (a)/(b) ratio is set at 8 or more), were obtained. For dogs, (D26) 3 kinds of dog whole duodenum (mucosa+muscle)-specific highly expressed genes comprising the base sequences shown by SEQ ID NO:11787 to 11789, respectively, (the (a)/(b) ratio is 8 or more) were obtained. Furthermore, for humans, (H21) 1 kind of human right atrium- and right ventricle-specific highly expressed gene comprising the base sequence shown by SEQ ID NO:11979 (the (a)/(b) ratio is 2 or more), (H22) 2 kinds of human left ventricle- and right ventricle-specific highly expressed genes comprising the base sequences shown by SEQ ID NO:11980 to 11981, respectively, (the (a)/(b) ratio is 4 or more), (H23) 2 kinds of human left atrium- and right atrium-specific highly expressed genes comprising the base sequences shown by SEQ ID NO:11982 to 11983, respectively, and (H24) 3 kinds of human whole heart (left atrium+right atrium+left ventricle+right ventricle)-specific highly expressed genes comprising the base sequences shown by SEQ ID NO:11984 to 11986, respectively, (hereinabove, the (a)/(b) ratio is set at 8 or more) were obtained.

A nucleic acid comprising the same or substantially the same base sequence as each base sequence shown by each SEQ ID NO given above or a partial sequence thereof can be prepared in the same manner as with a nucleic acid that constitutes another analytical tool for the expression of mouse, rat, dog or human organ- or tissue-specific genes.

In the specification, where bases, amino acids, etc. are denoted by their codes, they are based on conventional codes in accordance with the IUPAC-IUB Commission on Biochemical Nomenclature or by the common codes in the art, examples of which are shown below. For amino acids that may have the optical isomer, L form is presented unless otherwise indicated.

DNA: deoxyribonucleic acid
cDNA: complementary deoxyribonucleic acid
A: adenine
T: thymine
G: guanine
C: cytosine
RNA: ribonucleic acid
mRNA: messenger ribonucleic acid
DATP: deoxyadenosine triphosphate
dTTP: deoxythymidine triphosphate
dGTP: deoxyguanosine triphosphate
dCTP: deoxycytidine triphosphate
ATP: adenosine triphosphate
EDTA: ethylenediaminetetraacetic acid
SDS: sodium dodecyl sulfate The present invention is explained in more detail in the following by referring to Examples, which are not to be construed as limitative.

EXAMPLE 1

Materials and Methods

1. Database Used and Method of Data Extraction

Gene expression data on male C57BL/6 mice were extracted from BioExpress of GENE LOGIC™ on Apr. 21, 2006. The parameters used in the extraction are shown in Table 1. Mouse Genome 430 2.0 Array includes 45101 probe sets.

TABLE 1

Parameter settings at time of extraction of C57BL/6 mouse gene expression data

| Parameter setting in BioExpress | Parameter |
|---|---|
| Donor Species | M. musculus |
| Strain | C57BL/6 |
| Gender | Male |
| Chipset | Mouse430_2 (AFFYMETRIX™, Mouse Genome 430 2.0 Array) |
| Algorithm | MAS5.0 (AFFYMETRIX™) |
| Normalization | AFFYMETRIX™ |
| General Pathologic Category | Normal |
| IVT Labeling Protocol-Mouse430_2 | Double Biotin |

2. Method of Calculating Log-Ratio Values of the Gene Expression Data

The gene expression data extracted were subjected to a logarithmic conversion with the base 2 using the Avadis version 3.3 software program (manufactured by STRAND GENOMICS™). The mean of AFFX-GapdhMur/M32599_5_at, AFFX-GapdhMur/M32599_M_at, and AFFX-GapdhMur/M32599_3_at was subtracted from the value of each probe set, and this was used as the Log-ratio value. Fold change was set at $2^{(log\text{-}ratio\ value)}$.

3. Method of Extracting Tissue-Specific Highly Expressed Genes

Genes highly expressed specifically in various tissues were extracted according to the method described below. Using the gene expression data extracted, the highest Log-ratio value in other organs/tissues was subtracted from the lowest Log-ratio value of gene expression in the organ/tissue of interest; a probe set wherein the difference obtained was not less than 1 (Fold change=2 fold or more) was regarded as the desired tissue-specific highly expressed gene. Hence, the sample giving the lowest gene expression value for the tissue of interest exhibits not less than 2 fold higher expression than the sample giving the highest gene expression value for the other tissues. This was performed on each organ/tissue, and a gene highly expressed specifically in each organ/tissue was extracted. For tissues from which no specific highly expressed gene was obtained, they were combined with other tissues, and the same extraction was performed, whereby genes highly expressed specifically in the combination of organs/tissues were extracted.

[Results]

1. Data Used

The data used were extracted from the gene expression database BioExpress, introduced from GENE LOGIC™. A total of 20 organs/tissues had the data extracted therefrom: fat tissue, urinary bladder, blood, femoral bone, brain, mammary gland, colon, esophagus, heart, kidney (left), kidney (right), liver, lung, pancreas, prostate, skeletal muscle, spleen, stomach, testis, and thymus, the total number of samples being 72. The C57BL/6 mice used were at 39 days to 9 weeks of age; regarding the organs/tissues used, the least number of samples was 1 (pancreas) and the largest number of samples was 5 (fat tissue, prostate, skeletal muscle, testis). In the BioExpress of GENE LOGIC™, samples from other mouse strains are included; however, since the largest number of gene expression data sets (samples) was obtained for each organ from intact C57BL/6 mice, the mouse strain C57BL/6 was adopted.

2. Identification of Genes Highly Expressed Specifically in Various Mouse Organs/Tissues Using the above-described method of extracting a tissue-specific highly expressed gene, genes specifically expressed in various mouse organs/tissues were identified. The number of specific expression probe sets was 35 for fat tissue, 36 for urinary bladder, 431 for blood, 6 for femoral bone, 246 for brain, 17 for mammary gland, 52 for colon, 2 for esophagus, 23 for heart, 0 for kidney (left), 0 for kidney (right), 144 for liver, 143 for lung, 2970 for pancreas, 0 for prostate, 0 for skeletal muscle, 195 for spleen, 29 for stomach, 4669 for testis, and 141 for thymus 141 (Table 2). Since no tissue-specific expression probe set was obtained for kidney (left), kidney (right), prostate and skeletal muscle, the following investigation was performed.

TABLE 2

Numbers of genes highly expressed specifically in various organs/tissues

| Name of organ/tissue | Number of probe sets showing at least 2 folds or more higher expression than in other organs |
|---|---|
| Fat tissue | 35 |
| Urinary bladder | 36 |
| Blood | 431 |
| Femoral bone | 6 |
| Brain | 246 |
| Mammary gland | 17 |
| Colon | 52 |
| Esophagus | 2 |
| Heart | 23 |
| Kidney (left) | 0 |
| Kidney (right) | 0 |
| Liver | 144 |

TABLE 2-continued

Numbers of genes highly expressed specifically in various organs/tissues

| Name of organ/tissue | Number of probe sets showing at least 2 folds or more higher expression than in other organs |
|---|---|
| Lung | 143 |
| Pancreas | 2970 |
| Prostate | 0 |
| Skeletal muscle | 0 |
| Spleen | 195 |
| Stomach | 29 |
| Testis | 4669 |
| Thymus | 141 |

EXAMPLE 2

Figure 2:
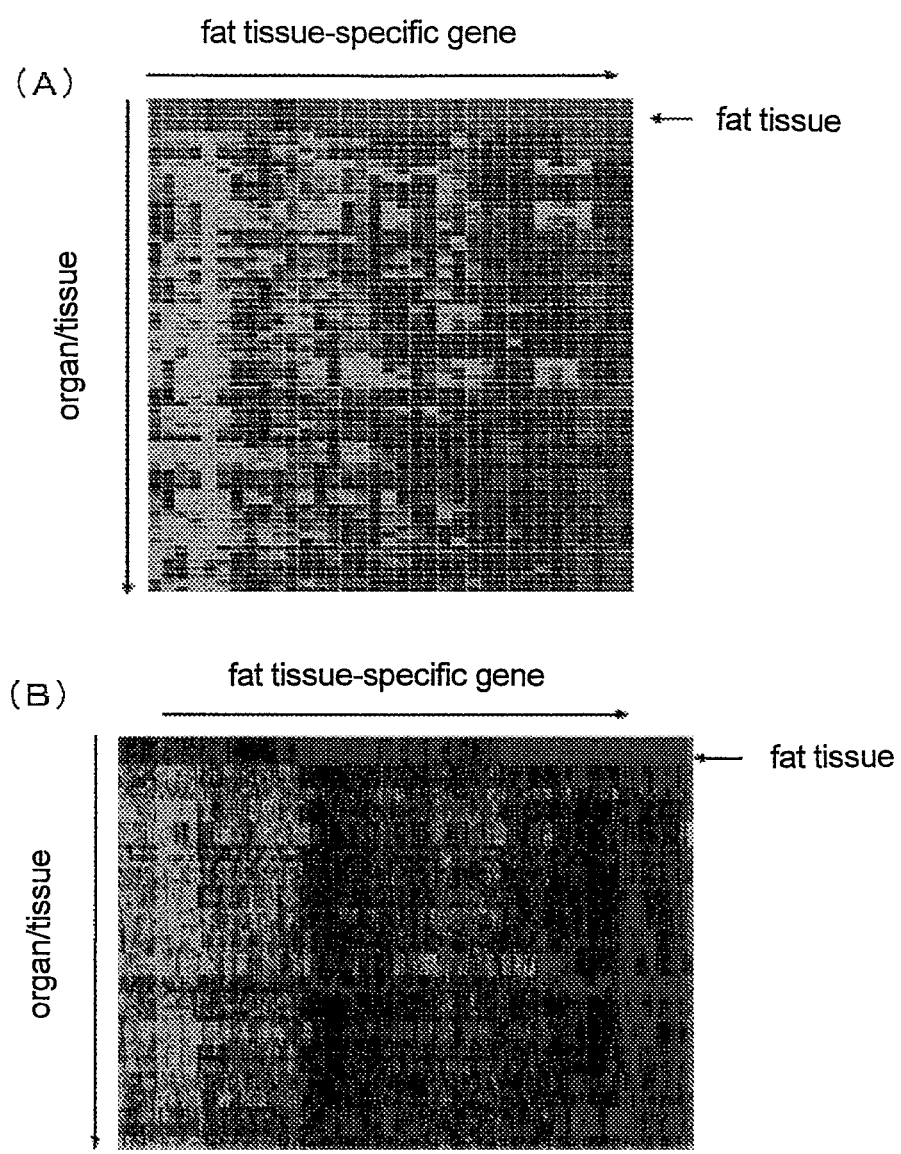
[FIG. 2] A graph showing the expression of the fat tissue specific highly expressed gene groups obtained in Example 1 (A) and Comparative Example (B) in various organs/tissues. Each column indicates a specific highly expressed gene extracted; each line, from the top, indicates each of various organs/tissues: fat tissue (n=5), urinary bladder (n=4), blood (n=2), femoral bone (n=4), brain (n=4), mammary gland (n=3), colon (n=4), esophagus (n=4), heart (n=4), left kidney (n=4), liver (n=4), lung (n=2), pancreas (n=1), prostate (n=5), right kidney (n=4), skeletal muscle (n=5), spleen (n=3), stomach (n=3), testis (n=5), and thymus (n=2).
Figure 3:
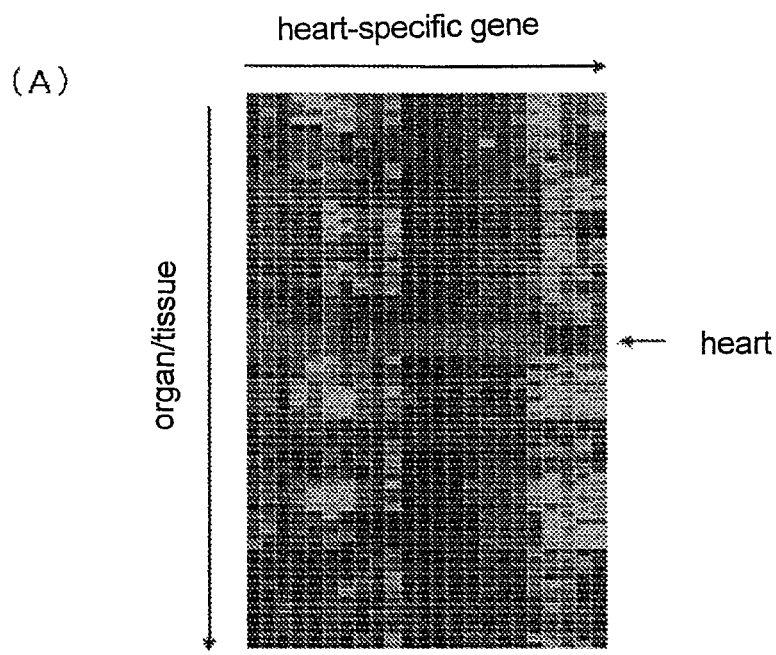
[FIG. 3] A graph showing the expression of the heart fat tissue specific highly expressed gene groups obtained in Example 1 (A) and Comparative Example (B) in various organs/tissues. Each column indicates a specific highly expressed gene extracted; each line, from the top, indicates each of various organs/tissues: fat tissue (n=5), urinary bladder (n=4), blood (n=2), femoral bone (n=4), brain (n=4), mammary gland (n=3), colon (n=4), esophagus (n=4), heart (n=4), left kidney (n=4), liver (n=4), lung (n=2), pancreas (n=1), prostate (n=5), right kidney (n=4), skeletal muscle (n=5), spleen (n=3), stomach (n=3), testis (n=5), and thymus (n=2).
Figure 3:
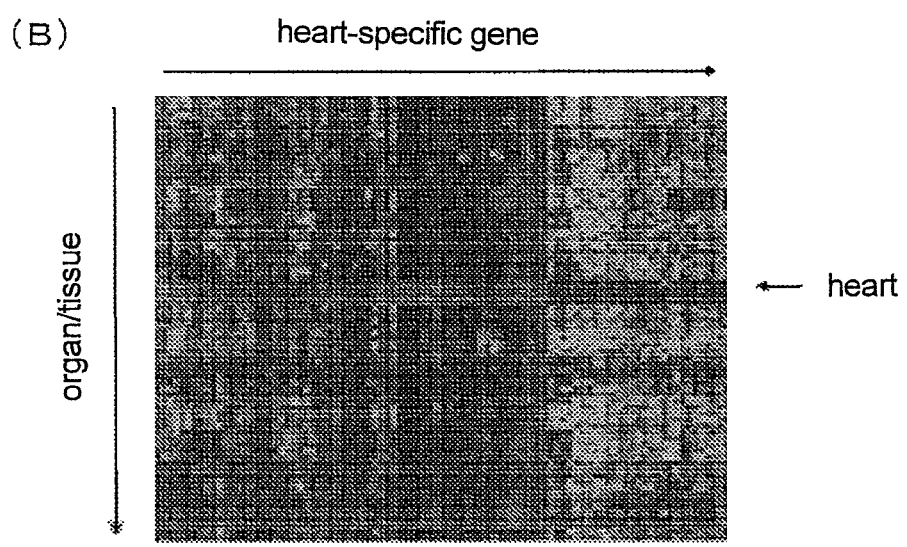
Figure 4:
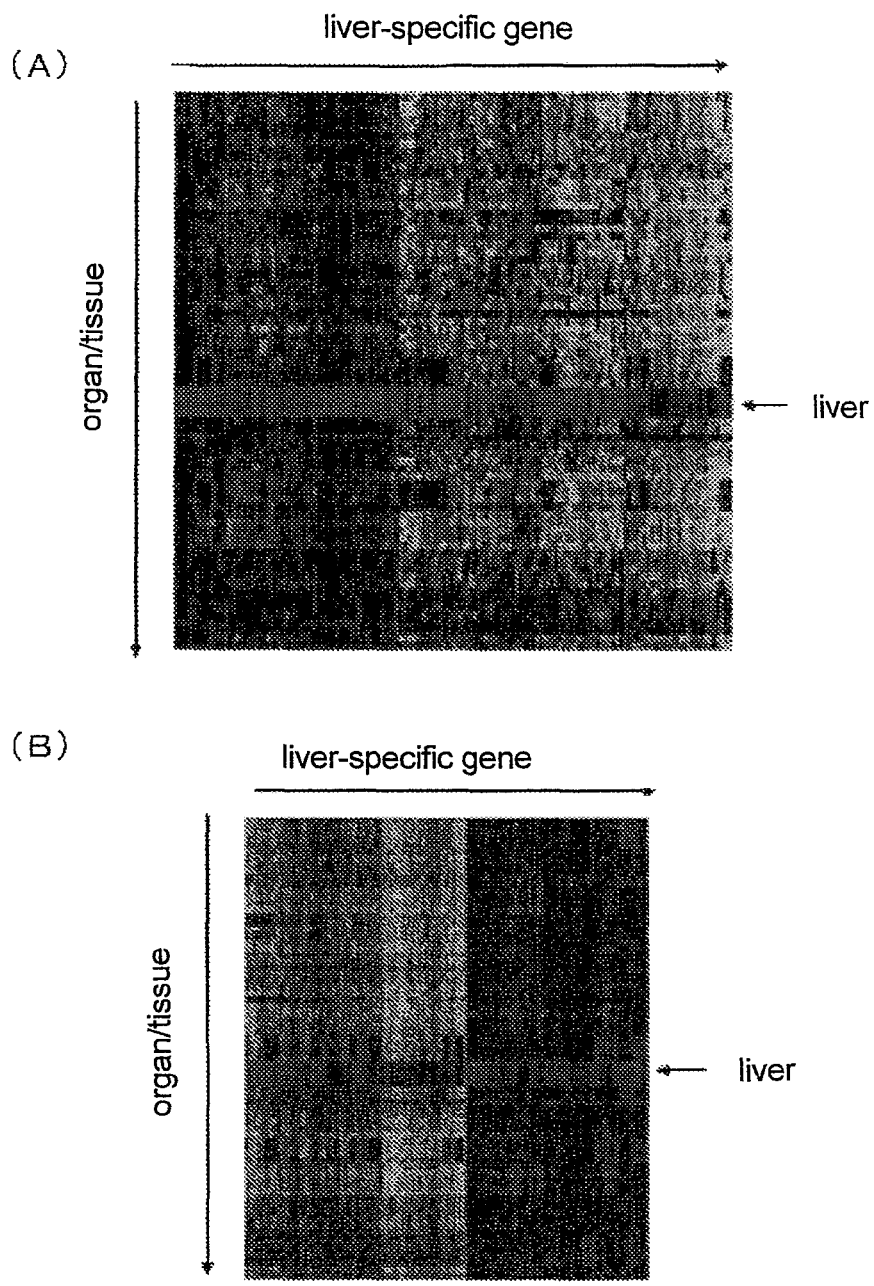
[FIG. 4] A graph showing the expression of the liver specific highly expressed gene groups obtained in Example 1 (A) and Comparative Example (B) in various organs/tissues. Each column indicates a specific highly expressed gene extracted; each line, from the top, indicates each of various organs/tissues: fat tissue (n=5), urinary bladder (n=4), blood (n=2), femoral bone (n=4), brain (n=4), mammary gland (n=3), colon (n=4), esophagus (n=4), heart (n=4), left kidney (n=4), liver (n=4), lung (n=2), pancreas (n=1), prostate (n=5), right kidney (n=4), skeletal muscle (n=5), spleen (n=3), stomach (n=3), testis (n=5), and thymus (n=2).
Figure 5:
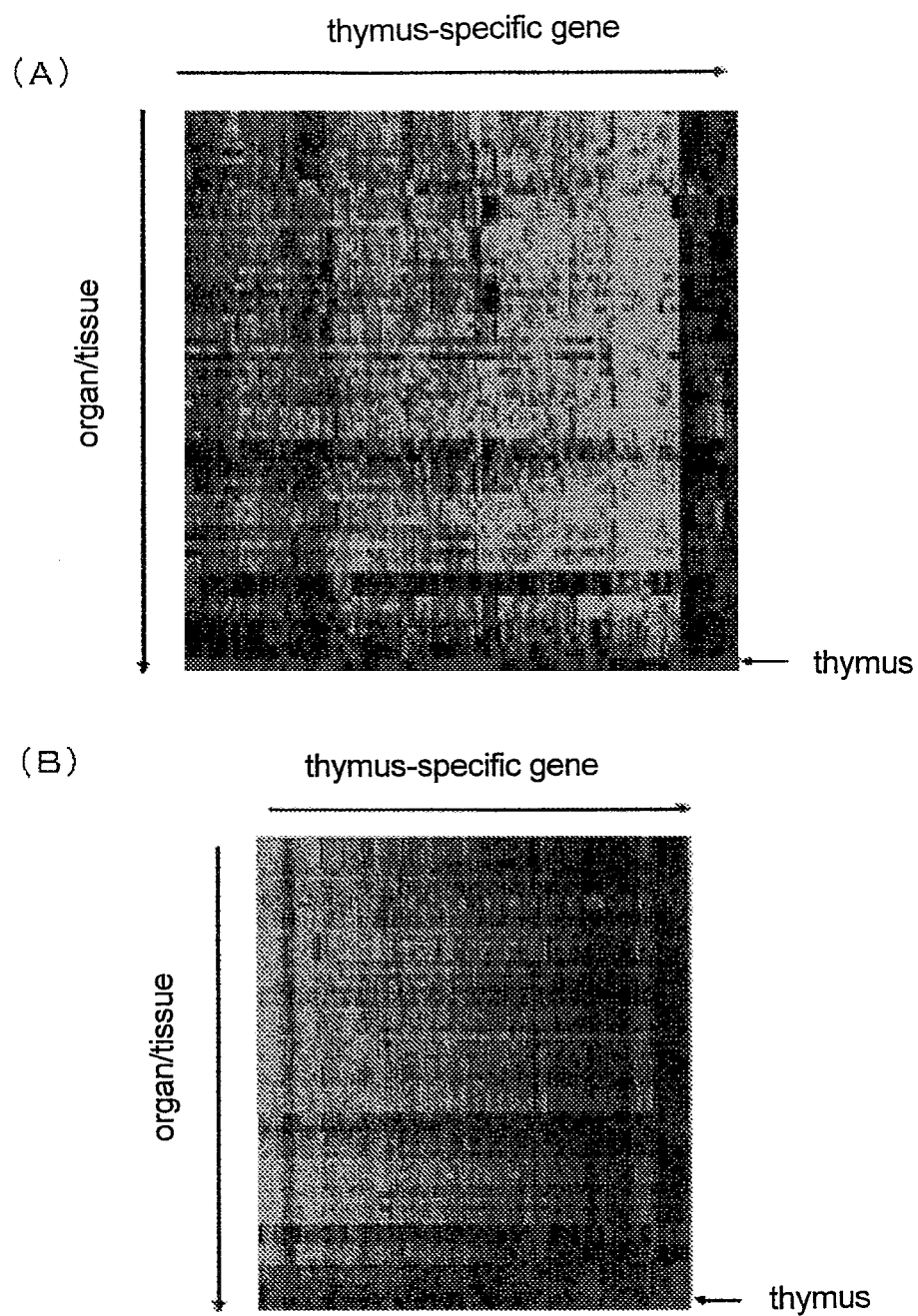
[FIG. 5] A graph showing the expression of the thymus specific highly expressed gene groups obtained in Example 1 (A) and Comparative Example (B) in various organs/tissues. Each column indicates a specific highly expressed gene extracted; each line, from the top, indicates each of various organs/tissues: fat tissue (n=5), urinary bladder (n=4), blood (n=2), femoral bone (n=4), brain (n=4), mammary gland (n=3), colon (n=4), esophagus (n=4), heart (n=4), left kidney (n=4), liver (n=4), lung (n=2), pancreas (n=1), prostate (n=5), right kidney (n=4), skeletal muscle (n=5), spleen (n=3), stomach (n=3), testis (n=5), and thymus (n=2).
Figure 6:
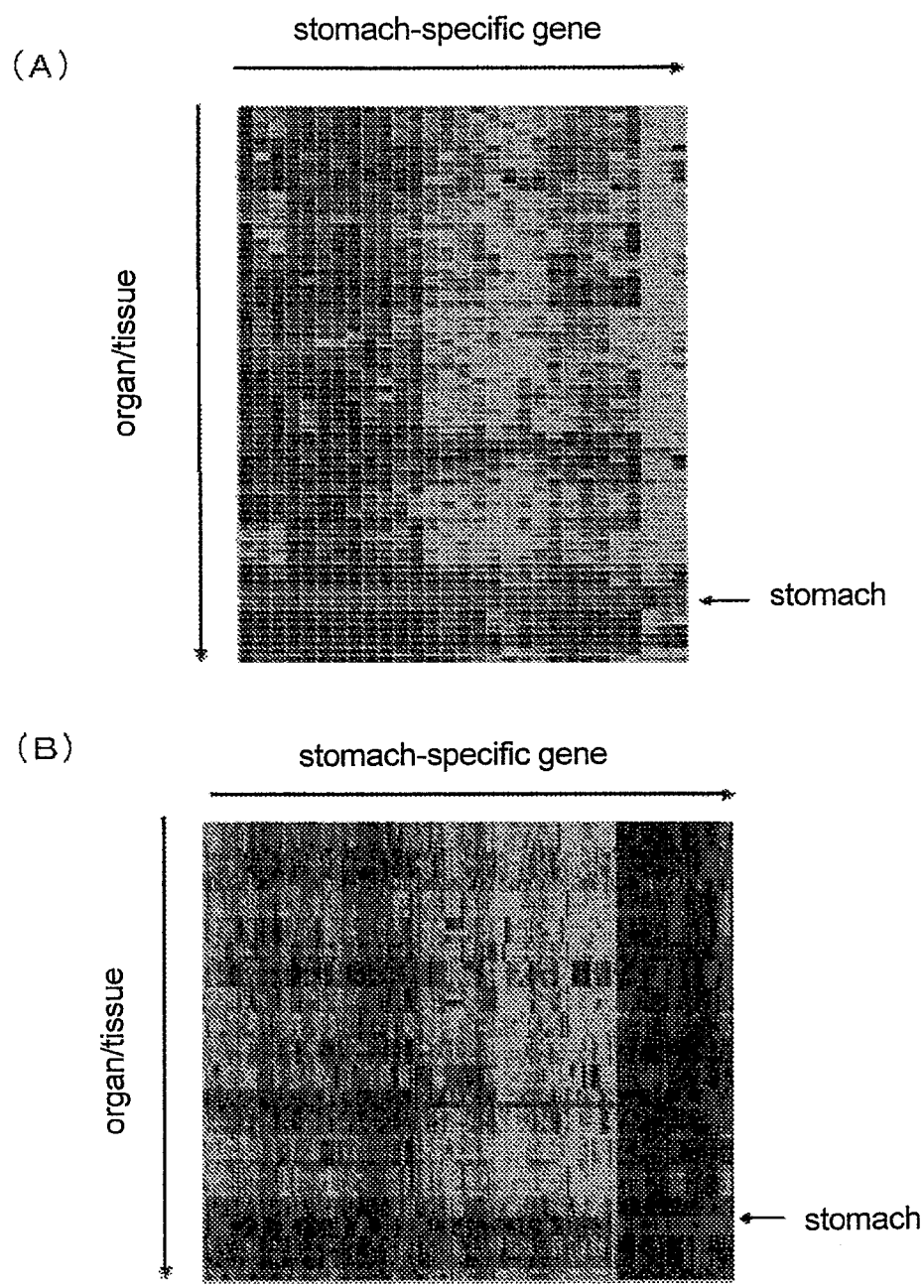
[FIG. 6] A graph showing the expression of the stomach specific highly expressed gene groups obtained in Example 1 (A) and Comparative Example (B) in various organs/tissues. Each column indicates a specific highly expressed gene extracted; each line, from the top, indicates each of various organs/tissues: fat tissue (n=5), urinary bladder (n=4), blood (n=2), femoral bone (n=4), brain (n=4), mammary gland (n=3), colon (n=4), esophagus (n=4), heart (n=4), left kidney (n=4), liver (n=4), lung (n=2), pancreas (n=1), prostate (n=5), right kidney (n=4), skeletal muscle (n=5), spleen (n=3), stomach (n=3), testis (n=5), and thymus (n=2).

Comparison of Organ/Tissue Specificity with Specific Genes Obtained by Other Method of Extraction The expression of the genes specific for various organs/tissues obtained in Example 1 and the expression of the organ/tissue-specific genes obtained by a method previously published by the present inventors (see the non-patent document 1 and FIG. 1) (Comparative Example) in various mouse organs/tissues were compared by generating heat maps. FIG. 2 shows a comparison of both for a fat tissue-specific gene group, FIG. 3 shows a comparison for a heart-specific gene group, FIG. 4 shows a comparison for a liver-specific gene group, FIG. 5 shows a comparison for a thymus-specific gene group, and FIG. 6 shows a comparison for a stomach-specific gene group (in all graphs, A represents the results from the gene groups obtained in Example 1, and B represents the results from the gene groups obtained in Comparative Example). For all organ/tissue-specific gene groups, almost all of the genes obtained in Example 1 had the expression thereof localized in the organs/tissues, whereas the genes obtained in Comparative Example included a considerable number of genes that were also highly expressed in other organs/tissues. This demonstrates that the method of the present invention of extracting organ/tissue-specific genes is better than the conventional method.

EXAMPLE 3

Identification of Genes Highly Expressed Specifically in Combinations of Organs/Tissues For the kidney (left), kidney (right), prostate and skeletal muscle, for which no specific highly expressed gene was identifiable in Example 1, an attempt was made to identify specific highly expressed genes using combinations with other organs/tissues. As a result, it was found that when the kidney (left) and the kidney (right) were combined, 66 probe sets were expressed specifically in the kidneys (left and right). For the prostate, it was found that when it was combined with the pancreas, 1 probe set was highly expressed specifically in the prostate/pancreas (Table 3). For skeletal muscle, an analysis was attempted after it was combined with the heart, which mainly consists of muscular tissue, or with the prostate, from which no specific gene was acquired when examined alone, but no specific highly expressed gene was acquired.

TABLE 3

Numbers of genes highly expressed specifically in combinations of organs/tissues

| Name of organ/tissue | Number of probe sets showing expression at least 2 folds or more higher than in other organs |
|---|---|
| Kidney (left) + kidney (right) | 66 |
| Pancreas + prostate | 1 |
| Skeletal muscle + heart | 0 |
| Skeletal muscle + prostate | 0 |

EXAMPLE 4

Analysis of Wistar Rat Organ-Specific Highly Expressed Genes

[Materials and Methods]

1. Database Used and Method of Data Extraction

Gene expression data on 13 organs (urinary bladder, cerebellum, colon, cerebral cortex frontal lobe, cerebral cortex parietal lobe, cerebral cortex temporal lobe, esophagus, heart, left kidney, left testis, liver, lung, stomach) from 2-month-old male Wistar rats were extracted from BioExpress of Gene Logic on Jul. 24, 2007. The parameters used in the extraction are shown in Table 4. Fourteen tissues not covered in BioExpress of GENE LOGIC™ (spleen, duodenum, jejunum, ileum, mesenteric lymph node, submandibular lymph node, thymus, pancreas, adrenal, skeletal muscle, mammary gland, femoral bone, prostate, fat tissue) and blood were collected from three 2-month-old male Wistar rats, RNAs were extracted using an RNA extraction kit from QIAGEN™, and RAE230 2.0 Array data were obtained according to the protocol of AFFYMETRIX™. The Rat Genome RAE230 2.0 Array includes 31099 probe sets.

TABLE 4

Parameter settings at time of extraction of Wistar rat gene expression data

| Parameter setting in BioExpress | Parameter |
|---|---|
| Donor Species | R. norvegicus |
| Strain | Wistar |
| Gender | Male |
| Chipset | RAE430_2 (AFFYMETRIX™, Rat Genome 230 2.0 Array) |
| Algorithm | MAS5.0 (AFFYMETRIX™) |
| Normalization | AFFYMETRIX™ |

2. Method of Calculating Log-Ratio Values of Gene Expression Data

The gene expression data extracted were subjected to a logarithmic conversion with the base 2 using the Avadis version 3.3 software program (manufactured by STRAND GENOMICS™). The value of 1367557_s_at, which is a probe set for GAPDH, was subtracted from the value of each probe set, and this value was used as the Log-ratio value. Fold change was set at $2^{(Log\text{-}ratio\ value)}$.

3. Method of Extracting Organ/Tissue-Specific Highly Expressed Genes

Organs/tissue-specific highly expressed genes were extracted according to the method described below. Using the gene expression data extracted, the highest Log-ratio value in other organs/tissues was subtracted from the lowest Log-ratio value of gene expression in the organ/tissue of interest; a probe set wherein the value obtained was not less than 1 (2, or 3) (Fold change=2 (4, or 8) fold or more) was regarded as the desired tissue-specific highly expressed gene. Hence, the sample giving the lowest gene expression value for the tissue of interest exhibits not less than 2 (4, or 8) fold higher expression than the sample giving the highest gene expression value for other tissues. This was performed on each organ/tissue, and genes highly expressed specifically in each organ/tissue were extracted. For tissues from which no specific highly expressed gene was obtained, they were combined with other tissues, and the same extraction was performed, whereby genes highly expressed specifically in the combination of organs/tissues were extracted.

[Results]

1. Data Used

The data used were extracted from the gene expression database BioExpress, introduced from GENE LOGIC™, or obtained by performing a microarray analysis on RNAs actually extracted from various rat organs/tissues. A total of 28 organs/tissues had the data extracted therefrom: urinary bladder, cerebellum, colon, cerebral cortex frontal lobe, cerebral cortex parietal lobe, cerebral cortex temporal lobe, esophagus, heart, left kidney, left testis, liver, lung, stomach, spleen, duodenum, jejunum, ileum, mesenteric lymph node, submandibular lymph node, thymus, pancreas, adrenal, skeletal muscle, mammary gland, femoral bone, prostate, fat tissue and blood, the total number of samples being 118. Regarding the organs/tissues used, the least number of samples was 3 and the largest number of samples was 10.

2. Identification of Genes Highly Expressed Specifically in the Various Rat Organs/Tissues Using the above-described method of extracting organ/tissue-specific highly expressed genes, genes specifically expressed in various rat organs/tissues were identified. For Fold changes of larger than 1 fold, 2 folds or more, 4 folds or more and 8 folds or more, the numbers of probe sets expressed specifically in the respective organs/tissues are shown in Table 5(A); the numbers of probe sets expressed specifically in the respective combinations of organs/tissues are shown in Table 5(B).

TABLE 5

| Organ/tissue | Number of samples | Larger than 1 | 2 folds or more | 4 folds or more | 8 folds or more |
|---|---|---|---|---|---|
| | | (A) | | | |
| Fat tissue | 3 | 119 | 25 | 0 | 0 |
| Adrenal | 3 | 145 | 46 | 16 | 5 |
| Urinary bladder | 4 | 88 | 16 | 4 | 2 |
| Blood | 3 | 98 | 27 | 0 | 0 |
| Cerebellum | 10 | 81 | 22 | 12 | 4 |
| Colon | 4 | 38 | 7 | 3 | 0 |
| Cerebral cortex frontal lobe | 7 | 2 | 0 | 0 | 0 |
| Cerebral cortex parietal lobe | 9 | 0 | 0 | 0 | 0 |
| Cerebral cortex temporal lobe | 7 | 0 | 0 | 0 | 0 |
| Duodenum | 3 | 10 | 1 | 0 | 0 |
| Esophagus | 4 | 49 | 16 | 6 | 1 |
| Femoral bone | 3 | 57 | 24 | 18 | 10 |
| Heart | 9 | 35 | 13 | 4 | 0 |
| Ileum | 3 | 174 | 18 | 6 | 2 |
| Jejunum | 3 | 33 | 0 | 0 | 0 |
| Kidney | 3 | 92 | 36 | 21 | 12 |
| Testis | 4 | 3773 | 2028 | 1076 | 598 |
| Liver | 3 | 253 | 162 | 93 | 49 |
| Lung | 4 | 293 | 78 | 26 | 7 |
| Mammary gland | 3 | 265 | 58 | 22 | 11 |

TABLE 5-continued

| Organ/tissue | Number of samples | Fold change | | |
|---|---|---|---|---|
| | | Larger than 1 | 2 folds or more | 4 folds or more | 8 folds or more |
| Mesenteric lymph node | 3 | 256 | 0 | 0 | 0 |
| Pancreas | 3 | 1728 | 333 | 90 | 33 |
| Prostate | 3 | 365 | 107 | 47 | 26 |
| Skeletal muscle | 3 | 102 | 36 | 3 | 1 |
| Spleen | 3 | 102 | 6 | 2 | 1 |
| Stomach | 5 | 40 | 26 | 21 | 10 |
| Submandibular lymph node | 3 | 71 | 6 | 3 | 2 |
| Thymus | 3 | 50 | 4 | 0 | 0 |
| (B) | | | | | |
| Ileum + jejunum | 6 | 48 | 1 | 0 | 0 |
| Mesenteric lymph node + submandibular lymph node | 6 | 185 | 3 | 0 | 0 |
| Ileum + jejunum + skeletal muscle | 9 | 1 | 0 | 0 | 0 |
| Ileum + jejunum + heart | 15 | 0 | 0 | 0 | 0 |
| Ileum + jejunum + skeletal muscle + heart | 18 | 0 | 0 | 0 | 0 |
| Ileum + jejunum + duodenum | 9 | 44 | 12 | 4 | 3 |
| Ileum + jejunum + duodenum + colon | 13 | 50 | 19 | 6 | 2 |
| Ileum + jejunum + duodenum + stomach | 14 | 1 | 0 | 0 | 0 |
| Ileum + jejunum + duodenum + esophagus | 13 | 0 | 0 | 0 | 0 |
| Whole cerebral cortex | 23 | 130 | 21 | 1 | 0 |
| Mesenteric lymph node + submandibular lymph node + thymus | 9 | 44 | 1 | 0 | 0 |

EXAMPLE 5

Analysis of Beagle Dog Organ Specific Highly Expressed Genes

[Materials and Methods]

1. Methods of Data Extraction and Acquisition 12-month-old male beagle dogs were exsanguinated under Nembutal anesthesia, tissues were extirpated, and RNAs were extracted using an RNA extraction kit from QIAGEN™. Using the RNAs extracted, data on Canain ver 2.0Array were obtained according to the protocol of AFFYMETRIX™.

2. Method of Calculating Log-Ratio Values of the Gene Expression Data

The gene expression data extracted were subjected to a logarithmic conversion with the base 2 using the Avadis version 3.3 software program (manufactured by STRAND GENOMICS™). Subtracted from the value of each probe set was a logarithmically converted mean of CfaAffx.23015.1.s1_x_at, CfaAffx.26731.1.s1_x_at and CfaAffx.13010.1.s1_x_at, which are probe sets for GAPDH, and this was used as the Log-ratio value. Fold change was set at $2^{(Log\text{-}ratio\ value)}$.

3. Method of Extracting Organ/Tissue-Specific Highly Expressed Genes

Organ/tissue-specific highly expressed genes were extracted according to the method described below. Using the gene expression data extracted, the highest Log-ratio value in other organs/tissues was subtracted from the lowest Log-ratio value of gene expression in the organ/tissue of interest; a probe set wherein the difference obtained was not less than 1 (2, or 3) (Fold change=2 (4, or 8) fold or more) was regarded as the desired tissue-specific highly expressed gene. Hence, the sample giving the lowest gene expression value for the tissue of interest exhibits not less than 2 (4, or 8) fold higher expression than the sample giving the highest gene expression value for the other tissues. This was performed on each organ/tissue, and a gene highly expressed specifically in each organ/tissue was extracted. For tissues from which no specific highly expressed gene was obtained, they were combined with other tissues, and the same extraction was performed, whereby genes highly expressed specifically in the combination of organs/tissues were extracted.

[Results]

1. Data Used

The data used were obtained by performing a microarray analysis on RNAs extracted from various beagle dog organs/tissues. A total of 35 organs/tissues had the data extracted therefrom: fat, adrenal, aorta, urinary bladder, cecum (mucosa), cecum (muscle), cerebral cortex, colon (mucosa), colon (muscle), duodenum (mucosa), duodenum (muscle), epididymis, heart, ileum (mucosa), ileum (muscle), jejunum (mucosa), jejunum (muscle), kidney (cortex), kidney (medulla), liver, lung, mesenteric lymph node, pancreas, hypophysis, rectum (mucosa), rectum (muscle), skeletal muscle, skin, spleen, stomach (mucosa), stomach (muscle), submandibular lymph node, testis, thymus, and thyroid, the total number of samples being 125. Regarding the organs/tissues used, the least number of samples was 2 and the largest number of is samples was 4.

2. Identification of Genes Highly Expressed Specifically in the Various Organs/Tissues Using the above-described method of extracting organ/tissue-specific highly expressed genes, genes specifically expressed in various beagle dog organs/tissues were identified. When the Fold change was set at larger than 1 fold, 2 folds or more, 4 folds or more and 8 folds or more, the numbers of probe sets expressed specifically in the respective organs/tissues are shown in Table 6(A); the numbers of probe sets expressed specifically in the respective combinations of organs/tissues are shown in Table 6(B).

TABLE 6

| Organ/tissue | Number of samples | Fold change | | |
|---|---|---|---|---|
| | | Larger than 1 | 2 folds or more | 4 folds or more | 8 folds or more |
| (A) | | | | | |
| Fat | 2 | 223 | 52 | 15 | 6 |
| Adrenal | 3 | 112 | 38 | 17 | 7 |
| Aorta | 4 | 180 | 35 | 1 | 0 |
| Urinary bladder | 4 | 5 | 1 | 1 | 0 |
| Cecum (mucosa) | 4 | 0 | 0 | 0 | 0 |
| Cecum (muscle) | 4 | 0 | 0 | 0 | 0 |

TABLE 6-continued

| Organ/tissue | Number of samples | Fold change | | | |
|---|---|---|---|---|---|
| | | Larger than 1 | 2 folds or more | 4 folds or more | 8 folds or more |
| Cerebral cortex | 4 | 437 | 159 | 63 | 10 |
| Colon (mucosa) | 4 | 3 | 0 | 0 | 0 |
| Colon (muscle) | 4 | 0 | 0 | 0 | 0 |
| Duodenum (mucosa) | 2 | 53 | 2 | 0 | 0 |
| Duodenum (muscle) | 3 | 0 | 0 | 0 | 0 |
| Epididymis | 4 | 101 | 65 | 46 | 32 |
| Heart | 4 | 64 | 27 | 15 | 4 |
| Ileum (mucosa) | 4 | 8 | 0 | 0 | 0 |
| Ileum (muscle) | 4 | 0 | 0 | 0 | 0 |
| Jejunum (mucosa) | 3 | 20 | 0 | 0 | 0 |
| Jejunum (muscle) | 4 | 0 | 0 | 0 | 0 |
| Kidney (cortex) | 4 | 140 | 52 | 21 | 10 |
| Kidney (medulla) | 4 | 72 | 16 | 6 | 0 |
| Liver | 4 | 541 | 306 | 181 | 118 |
| Lung | 4 | 313 | 67 | 19 | 10 |
| Mesenteric lymph node | 4 | 77 | 3 | 1 | 0 |
| Pancreas | 2 | 2770 | 824 | 191 | 90 |
| Hypophysis | 4 | 133 | 29 | 8 | 3 |
| Rectum (mucosa) | 3 | 0 | 0 | 0 | 0 |
| Rectum (muscle) | 4 | 2 | 0 | 0 | 0 |
| Skeletal muscle | 4 | 123 | 58 | 38 | 24 |
| Skin | 3 | 412 | 166 | 92 | 53 |
| Spleen | 4 | 461 | 86 | 30 | 5 |
| Stomach (mucosa) | 2 | 194 | 45 | 19 | 12 |
| Stomach (muscle) | 2 | 40 | 5 | 0 | 0 |
| Submandibular lymph node | 4 | 165 | 64 | 28 | 11 |
| Testis | 4 | 6799 | 4070 | 2337 | 1303 |
| Thymus | 4 | 198 | 46 | 14 | 2 |
| Thyroid | 4 | 117 | 33 | 15 | 14 |
| Whole cecum (mucosa + muscle) | 8 | 0 | 0 | 0 | 0 |
| Whole colon (mucosa + muscle) | 8 | 0 | 0 | 0 | 0 |
| Whole duodenum (mucosa + muscle) | 5 | 3 | 3 | 3 | 3 |
| Whole ileum (mucosa + muscle) | 8 | 5 | 2 | 1 | 1 |
| Whole jejunum (mucosa + muscle) | 7 | 0 | 0 | 0 | 0 |
| Whole rectum (mucosa + muscle) | 7 | 0 | 0 | 0 | 0 |
| Stomach (mucosa + muscle) | 4 | 1 | 0 | 0 | 0 |
| Whole mucosa | 22 | 0 | 0 | 0 | 0 |
| Whole muscle | 25 | 0 | 0 | 0 | 0 |
| (B) | | | | | |
| Cecum + rectum (mucosa) | 7 | 0 | 0 | 0 | 0 |
| Cecum + rectum + colon (mucosa) | 11 | 2 | 0 | 0 | 0 |
| Cecum + rectum (muscle) | 8 | 0 | 0 | 0 | 0 |
| Cecum + rectum + colon (muscle) | 12 | 0 | 0 | 0 | 0 |
| Duodenum + ileum + jejunum (mucosa) | 9 | 11 | 0 | 0 | 0 |
| Duodenum + ileum + jejunum (muscle) | 11 | 0 | 0 | 0 | 0 |
| Stomach (mucosa) + submandibular lymph node | 6 | 4 | 0 | 0 | 0 |
| Whole muscle (except ileum) + urinary bladder | 25 | 0 | 0 | 0 | 0 |
| Ileum + jejunum (mucosa) | 7 | 5 | 0 | 0 | 0 |
| Ileum + jejunum (muscle) | 8 | 0 | 0 | 0 | 0 |

EXAMPLE 6

Analysis of Human Organ Specific Highly Expressed Genes

[Materials and Methods]

1. Database Used and Method of Data Extraction

Using GENE LOGIC™ BioExpress, gene expression data on 31 organs or tissues from 35- to 55-year-old men were extracted on Sep. 19, 2007 (fat, aorta, urinary bladder, body of the stomach, osteous tissue, cecum, cerebellum, cerebrum, colon, duodenum, esophagus, heart (left atrium, right atrium, left ventricle, right ventricle), hypothalamus, ileum, jejunum, kidney, liver, lung, pancreas, prostate, rectum, skeletal muscle, skin, spleen, testis, thalamus, thyroid, vein). The organs/tissues used had been confirmed as normal in pathological examination.

2. Method of Calculating Log-Ratio Values of Gene Expression Data

The gene expression data extracted were subjected to a logarithmic conversion with the base 2 using the Avadis version 3.3 software program (manufactured by STRAND GENOMICS)™. Subtracted from the value of each probe set was a logarithmically converted mean of 212581_x_at, 213453_x_at and 217398_x_at, which are probe sets for GAPDH, and this was used as the Log-ratio value. Fold change was set at $2^{(log\text{-}ratio\ value)}$.

3. Method of Extracting Tissue-Specific Highly Expressed Genes

Organ/tissue-specific highly expressed genes were extracted according to the method described below. Using the gene expression data extracted, the highest Log-ratio value in other organs/tissues was subtracted from the lowest Log-ratio value of gene expression in the organ/tissue of interest; a probe set wherein the difference obtained was not less than 1 (2, or 3) (Fold change=2 (4, or 8) fold or more) was regarded as the desired tissue-specific highly expressed gene. Hence, the sample giving the lowest gene expression value for the tissue of interest exhibits not less than 2 (4, or 8) fold higher expression than the sample giving the highest gene expression value for the other tissues. This was performed on each organ/tissue, and a gene highly expressed specifically in each organ/tissue was extracted. For tissues from which no specific highly expressed gene was obtained, they were combined with other tissues, and the same extraction was performed, whereby genes highly expressed specifically in the combination of organs/tissues were extracted.

[Results]

1. Data Used

The data used were extracted from the gene expression database BioExpress, introduced from GENE LOGIC™. A total of 31 organs/tissues had the data extracted therefrom: fat, aorta, urinary bladder, body of the stomach, osteous tissue, cecum, cerebellum, cerebrum, colon, duodenum, esophagus, heart (left atrium, right atrium, left ventricle, right ventricle), hypothalamus, ileum, jejunum, kidney, liver, lung, pancreas, prostate, rectum, skeletal muscle, skin, spleen, testis, thalamus, thyroid, and vein, the total number of samples being 100. Regarding the organs/tissues used, the least number of samples was 1 and the largest number of samples was 9.

2. Identification of Genes Highly Expressed Specifically in Various Organs/Tissues Using the above-described method of extracting organ/tissue-specific highly expressed genes, genes expressed specifically in various human organs/tissues were identified. When the Fold change was set at larger than 1 fold, 2 folds or more, 4 folds or more and 8 folds or more, the numbers of probe sets expressed specifically in the respective organ/tissues are shown in Table 7(A); the numbers of probe sets expressed specifically in the respective combinations of organs/tissues are shown in Table 7(B).

TABLE 7

| Organ/tissue | Number of samples | Larger than 1 | 2 folds or more | 4 folds or more | 8 folds or more |
|---|---|---|---|---|---|
| (A) | | | | | |
| Fat | 2 | 0 | 0 | 0 | 0 |
| Aorta | 1 | 222 | 17 | 0 | 0 |
| Urinary bladder | 1 | 76 | 8 | 1 | 0 |
| Body of the | 3 | 1 | 0 | 0 | 0 |
| Osteous tissue | 1 | 216 | 39 | 16 | 8 |
| Cecum | 3 | 1 | 0 | 0 | 0 |
| Cerebellum | 2 | 442 | 95 | 20 | 3 |
| Cerebrum | 1 | 774 | 108 | 19 | 0 |
| Colon | 6 | 0 | 0 | 0 | 0 |
| Duodenum | 8 | 0 | 0 | 0 | 0 |
| Esophagus | 3 | 0 | 0 | 0 | 0 |
| Hypothalamus | 5 | 49 | 8 | 0 | 0 |
| Ileum | 4 | 0 | 0 | 0 | 0 |
| Jejunum | 5 | 0 | 0 | 0 | 0 |
| Kidney | 7 | 117 | 51 | 29 | 12 |
| Liver | 4 | 113 | 33 | 13 | 5 |
| Lung | 9 | 193 | 45 | 26 | 19 |
| Pancreas | 2 | 864 | 143 | 57 | 45 |
| Prostate | 9 | 17 | 11 | 4 | 4 |
| Rectum | 1 | 18 | 0 | 0 | 0 |
| Skeletal muscle | 8 | 87 | 49 | 23 | 14 |
| Skin | 3 | 55 | 24 | 16 | 5 |
| Spleen | 2 | 419 | 80 | 6 | 1 |
| Testis | 2 | 258 | 79 | 26 | 10 |
| Thalamus | 1 | 245 | 26 | 3 | 0 |
| Thyroid | 1 | 73 | 23 | 11 | 10 |
| Vein | 2 | 8 | 0 | 0 | 0 |
| Left atrium | 1 | 19 | 0 | 0 | 0 |
| Right atrium | 1 | 33 | 1 | 1 | 1 |
| Left ventricle | 1 | 356 | 37 | 1 | 0 |
| Right ventricle | 1 | 64 | 3 | 0 | 0 |
| (B) | | | | | |
| Ileum + jejunum | 9 | 0 | 0 | 0 | 0 |
| Ileum + jejunum + duodenum | 17 | 1 | 0 | 0 | 0 |
| Colon + rectum | 7 | 0 | 0 | 0 | 0 |
| Cecum + colon + rectum | 10 | 0 | 0 | 0 | 0 |
| Stomach + esophagus | 6 | 0 | 0 | 0 | 0 |
| Aorta + vein | 3 | 10 | 0 | 0 | 0 |
| Left atrium + right atrium | 2 | 11 | 7 | 3 | 2 |
| Left ventricle + right ventricle | 2 | 82 | 8 | 2 | 0 |
| Left atrium + left ventricle | 2 | 8 | 0 | 0 | 0 |
| Right atrium + right ventricle | 2 | 16 | 1 | 0 | 0 |
| Whole heart | 4 | 41 | 13 | 5 | 3 |

INDUSTRIAL APPLICABILITY

The method of the present invention for extracting an organ- or tissue-specific gene enables the extraction of a set of truly organ- or tissue-specific highly expressed genes, and is useful as a tool for searching disease markers and toxicity markers in each organ/tissue. The method of the present invention for identifying an unidentified organ or tissue enables the identification of an organ or tissue for which no specific highly expressed gene has been obtained, and is useful in, for example, confirming differentiation in the field of regenerative medicine and the like.

While the present invention has been described with emphasis on preferred embodiments, it is obvious to those skilled in the art that the preferred embodiments can be modified. The present invention intends that the present invention can be embodied by methods other than those described in detail in the present specification. Accordingly, the present invention encompasses all modifications encompassed in the gist and scope of the appended "CLAIMS."

This application is based on patent application No. 2006-293324 filed on Oct. 27, 2006 in Japan, and the contents disclosed therein are hereby entirely incorporated by reference. In addition, the contents disclosed in any publication cited herein, including patents and patent applications, are hereby incorporated in their entireties by reference, to the extent that they have been disclosed herein.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08535880B2). An electronic copy of the "Sequence Listing" will also be available from the USPTO upon request and payment of the fee set forth in 37 CFR 1.19(b)(3).

The invention claimed is:

1. A method of identifying or not identifying an organ- or tissue-specific highly expressed gene, comprising the steps (1) to (4) below;
   (1) providing 2 or more samples of gene transcripts from each of organs or tissues including fat tissue, urinary bladder, blood, femoral bone, brain, spinal cord, hypophysis, thyroid, gallbladder, bone marrow, adrenal, skin, blood vessels, mammary gland, colon, esophagus, heart, kidney, liver, lung, pancreas, prostate, skeletal muscle, spleen, stomach, testis, thymus, ovary, placenta and uterus,
   wherein the samples of gene transcripts from each organ or tissue are isolated from different individuals,
   (2) measuring expression levels of a specified gene group for all of the samples,
   (3) acquiring, for each gene, (a) a minimum value of expression levels in said 2 or more samples from a particular organ or tissue and (b) a maximum value of expression levels in all said 2 or more samples from the other organs and tissues,
   (4) identifying the gene as a gene highly expressed specifically in the particular organ or tissue if the above-described (a)/(b) ratio is larger than 1 or not identifying the gene if said (a)/(b) ratio is not larger than 1.

2. The method of claim 1, wherein the gene is identified as a gene highly expressed specifically in a particular organ or tissue if the (a)/(b) ratio is not less than a given value between 2 and 8 or not identified if the (a)/(b) ratio is less than the given value in step (4) of claim 1.

3. A method of identifying an organ or tissue from which no specific highly expressed gene is identified by the method of claim 1, further comprising the steps shown below;
   (5) acquiring, for each gene,
      (a) a minimum value of expression levels in said 2 or more samples from an organ or tissue in which no specific highly expressed gene has been identified in step (4) of claim 1 and expression levels in said 2 or more samples from another particular organ or tissue in which a specific highly expressed gene has been identified in step (4) of claim 1, and
      (b) a maximum value of expression levels in all said 2 or more samples from organs and tissues other than each organ or tissue (a) above,
   (6) identifying the gene as a gene highly expressed specifically in each organ or tissue (a) above if the above-described (a)/(b) ratio is larger than 1,
   (7) measuring expression levels of (i) a gene highly expressed specifically in the other particular organ or tissue and (ii) the specific highly expressed gene identified in the above-described (6) in an unidentified organ or tissue,
   (8) identifying the unidentified organ or tissue as said organ or tissue from which the specific highly expressed gene is not identified, with the expression levels of the specific highly expressed genes of the above-described (i) and (ii) as indexes.

4. The method of claim 3, wherein the organ or tissue is derived from a mammal.

5. The method of claim 4, wherein the organ or tissue is derived from a human or mouse.

6. A method of identifying an organ or tissue from which no specific highly expressed gene is identified by the method of claim 2, further comprising the steps shown below;
   (5) acquiring, for each gene,
      (a) a minimum value of expression levels in said 2 or more samples from an organ or tissue in which no specific highly expressed gene has been identified in claim 2 and expression levels in said 2 or more samples from another particular organ or tissue in which a specific highly expressed gene has been identified in claim 2, and
      (b) a maximum value of expression levels in all said 2 or more samples from organs and tissues other than each organ or tissue (a) above,
   (6) extracting identifying the gene as a gene highly expressed specifically in each organ or tissue (a) above if the above-described (a)/(b) ratio is not less than the given value,
   (7) measuring expression levels of (i) a gene highly expressed specifically in the other particular organ or tissue and (ii) the specific highly expressed gene identified in the above-described (6) in an unidentified organ or tissue, and
   (8) identifying the unidentified organ or tissue as said organ or tissue from which the specific highly expressed gene is not identified, with the expression levels of the specific highly expressed genes of the above described (i) and (ii) as indexes.

7. The method of claim 6, wherein the organ or tissue is derived from a mammal.

8. The method of claim 7, wherein the organ or tissue is derived from a human or mouse.

* * * * *

UNITED STATES PATENT AND TRADEMARK OFFICE
CERTIFICATE OF CORRECTION

PATENT NO.        : 8,535,880 B2
APPLICATION NO.   : 12/447446
DATED             : September 17, 2013
INVENTOR(S)       : Saku Miyamoto, Kenji Takami and Akira Horinouchi It is certified that error appears in the above-identified patent and that said Letters Patent is hereby corrected as shown below:

In the Claims

Column 30, Line 29: Claim 6: delete "extracting"

Signed and Sealed this
Twenty-seventh Day of May, 2014

Michelle K. Lee
*Deputy Director of the United States Patent and Trademark Office*